US007947264B2

(12) United States Patent
Ferguson et al.

(10) Patent No.: US 7,947,264 B2
(45) Date of Patent: May 24, 2011

(54) TGF-β3 MUTANTS

(75) Inventors: Mark William James Ferguson, Manchester (GB); Phillip Mellors, Manchester (GB); Hugh Gerard Laverty, Manchester (GB); Nick Occleston, Manchester (GB); Sharon O'Kane, Manchester (GB); Emma Atkinson, Manchester (GB)

(73) Assignee: Renovo Limited, Manchester (GB)

( * ) Notice: Subject to any disclaimer, the term of this patent is extended or adjusted under 35 U.S.C. 154(b) by 225 days.

(21) Appl. No.: 12/282,463

(22) PCT Filed: Mar. 12, 2007

(86) PCT No.: PCT/GB2007/000833
§ 371 (c)(1),
(2), (4) Date: Sep. 10, 2008

(87) PCT Pub. No.: WO2007/104945
PCT Pub. Date: Sep. 20, 2007

(65) Prior Publication Data
US 2009/0105146 A1      Apr. 23, 2009

(30) Foreign Application Priority Data
Mar. 11, 2006  (GB) .................................. 0604938.1

(51) Int. Cl.
*A61K 38/19*     (2006.01)
*C07K 14/52*     (2006.01)
(52) U.S. Cl. .................................... 424/85.1; 530/351
(58) Field of Classification Search .......................... None
See application file for complete search history.

(56) References Cited

U.S. PATENT DOCUMENTS

| | | | |
|---|---|---|---|
| 4,051,848 A | 10/1977 | Levine | |
| 5,135,915 A | 8/1992 | Czarniecki et al. | |
| 5,411,940 A | 5/1995 | Nixon et al. | |
| 5,650,494 A | 7/1997 | Cerletti et al. | |
| 5,922,846 A | 7/1999 | Cerletti et al. | |
| 5,958,411 A | 9/1999 | Logan et al. | |
| 6,054,122 A | 4/2000 | MacPhee et al. | |
| 6,057,430 A | 5/2000 | Cerletti | |
| 6,132,759 A | 10/2000 | Schacht et al. | |
| 6,331,298 B1 | 12/2001 | Ferguson et al. | |
| 6,559,123 B1 | 5/2003 | Iwata et al. | |
| 6,972,321 B1 | 12/2005 | Hotten et al. | |
| 7,341,994 B2 | 3/2008 | Ishikawa et al. | |
| 7,691,816 B2 | 4/2010 | Ferguson et al. | |
| 2004/0078851 A1 | 4/2004 | Huang et al. | |

FOREIGN PATENT DOCUMENTS

| | | |
|---|---|---|
| EP | 0200341 | 11/1986 |
| EP | 0 433 225 | 6/1991 |
| EP | 0891985 | 1/1999 |
| EP | 0 943 690 | 9/1999 |
| EP | 1557468 A2 | 7/2005 |
| WO | WO90/03812 | 4/1990 |
| WO | WO-91/05565 | 5/1991 |
| WO | WO93/19769 | 10/1993 |
| WO | WO-95/16034 | 6/1995 |
| WO | WO96/03432 | 2/1996 |
| WO | WO96/32131 | 10/1996 |
| WO | WO-97/05166 | 2/1997 |
| WO | WO-99/18196 | 4/1999 |
| WO | WO-00/20607 | 4/2000 |
| WO | WO-0020612 A2 | 4/2000 |
| WO | WO00/54797 | 9/2000 |
| WO | WO-0056879 A1 | 9/2000 |
| WO | WO-0175132 A2 | 10/2001 |
| WO | WO-01/92298 | 12/2001 |
| WO | WO 01/92298 A2 * | 12/2001 |
| WO | WO-02/12336 | 2/2002 |
| WO | WO02/076494 | 10/2002 |
| WO | WO-02099067 A2 | 12/2002 |
| WO | WO-2006/023782 | 3/2006 |
| WO | WO-2006118617 A2 | 11/2006 |
| WO | WO-2007/007098 | 1/2007 |
| WO | WO-2007/104934 | 9/2007 |
| WO | WO-2007/104946 | 9/2007 |
| WO | WO-2008/032035 | 3/2008 |

OTHER PUBLICATIONS

Ejima et al., "A Novel 'Reverse Screening' to Identify Refolding Additives for Activin-A," Science Direct, Protein Expression and Purification, vol. 47 (2006), pp. 45-51; and online Sep. 20, 2005.
International Search Report for PCT/GB2007/003416, mailed Dec. 18, 2007.
International Search Report for PCT/GB2007/00814, mailed Nov. 7, 2007.
International Search Report for PCT/GB2007/00833, mailed Mar. 14, 2008.
International Search Report for PCT/GB2007/00834, mailed Apr. 3, 2008.
O'Kane et al. "Transforming Growth Factor βs and Wound Healing" Int. J. Biochem. Cell Biol. vol. 29, No. 1, pp. 63-78 (1997).
Schmid et al. "TGF-βs and TGF-β Type II Receptor in Human Epidermis: Differential Expression in Acute and Chronic Skin Wounds" J. of Pathology, vol. 171, pp. 191-197 (993).
Vallejo et al. "Optimized procedure for renaturation of recombinant human bone morphogenetic protein-2 at high protein concentration," Biotechnology and Bioengineering, Interscience Publishers, London, GB, vol. 85, No. 6., pp. 601-609.

(Continued)

*Primary Examiner* — Prema Mertz
(74) *Attorney, Agent, or Firm* — McDermott Will & Emery LLP

(57) ABSTRACT

The invention provides TGF-β3s, or fragments or derivatives thereof, wherein the alpha-helix-forming domain between amino acid residues (58) and (67) of full-length wild type TGF-β3 comprises at least one alpha-helix-stabilizing substitution. The invention also provides TGF-β3s, or fragments or derivatives thereof, wherein the Glycine residue at position (63) of full-length wild type TGF-β3 is replaced with Proline. Further still, the invention provides TGF-β3s, or fragments or derivatives thereof, comprising a substitution of the Glutamic acid residue at position (12) of full-length wild type TGF-β3 and/or the Arginine residue at position (52) of full-length wild type TGF-β3. The invention also provides medicaments and methods of treatment using such TGF-β3s.

8 Claims, 17 Drawing Sheets

OTHER PUBLICATIONS

Vallejo et al. "Renaturation and purification of bone morphogenetic protein-2 produced as inclusion bodies in high-cell density cultures of recombinant *Escherichia coli*," J. of Biotech., Elsevier Science Publishes B.V., Amsterdam, NL vol. 94, No. 2., pp. 185-194.

Bowie et al., "Deciphering the Message in Protein Sequences: Tolerance to Amino Acid Substitutions," *Science*, vol. 247, No. 4948, pp. 1306-1310 (1990).

Brannon, "Skin Anatomy," dermatology.about.com/cs/skinanatomy/a/anatomy.htm, downloaded Aug. 16, 2009.

Hao et al., TGF-$\beta$3: "A promising growth factor in engineered organogenesis," *Expert Opin. Boil. Ther.*, vol. 8, No. 10, pp. 1485-1493 (2008).

Hirshberg, 'TGF-$\beta$3 in the Treatment of Pressure Ulcers: A Preliminary Report, *Advances in Skin & Wound Care*, vol. 14, No. 2, pp. 91-95, www.woundcarenet.com (Mar./Apr. 2001).

International Search Report for WO2007/007098 (PCT/GB2006/002577) dated Mar. 3, 2007 (4 pages).

Martin, "Wound Healing—Aiming for Perfect Skin Regeneration," *Science*, vol. 276, pp. 75-81 (1997).

Ngo et al., "Computational Complexity, Protein Structure Prediction, and the Levinthal Paradox," *The Protein Folding Problem and Tertiary Structure Prediction*, Merz et al, eds, Birkhauser, Boston, pp. 433-506 (1994).

Schmid et al., "TGF-$\beta$s and TGF-$\beta$ Type II Receptor in Human Epidermis: Differential Expression in Acute and Chronic Skin Wounds," *Journal of Pathology*, vol. 171, pp. 191-197 (1993).

Shah et al., "Neutralisation of TGF-$\beta_1$ and TGF-$\beta_2$ or exogenous addition of TGF-$\beta_3$ to cutaneous rat wounds reduces scarring," *Journal of Cell Science*, vol. 108, pp. 985-1002 (1995).

Singer et al., "Cutaneous Wound Healing," *The New England Journal of Medicine*, vol. 341, No. 10, pp. 738-746 (1999).

Tyrone et al., "Transforming Growth Factor $\beta_3$ Promotes Fascial Wound Healing in a New Animal Model," *Arch. Surg.*, vol. 135, pp. 1154-1159, www.archsurg.com, (Oct. 2000).

U.S. Appl. No. 11/995,380: File History of all prosecution documents to date, including Bibliographic Data Page And Image File Wrapper Pages from PAIR as downloaded on Aug. 3, 2010.

U.S. Appl. No. 12/282,456: Non-Final Office Action dated Oct. 21, 2009, including Form PTO-892 (documents cited therein included by reference) (7 pages).

U.S. Appl. No. 12/282,456: Final Office Action dated May 26, 2010 (8 pages).

U.S. Appl. No. 12/282,472: File History of all prosecution documents to date, including Bibliographic Data Page and Image File Wrapper Pages from PAIR as downloaded on Aug. 3, 2010.

U.S. Appl. No. 12/440,688: File History of all prosecution documents to date, including Bibliographic Data Page and Image File Wrapper Pages from PAIR as downloaded on Aug. 3, 2010.

Vooijs et al., "Transforming growth factor-$\beta_3$ loaded microtextured membranes for skini regeneration in dermal wounds," *Journal of biomedical Materials Research*, vol. 70, No. 3, pp. 402-411 (2004).

Wang et al., "A Single Amino Acid Determines Lysophospholipid Specificity of the $S1P_1$(EDG1) and $LPA_1$ (EDG2) Phospholipid Growth Factor Receptors," *The Journal of Biological Chemistry*, vol. 276, No. 52, pp. 49213-49220 (2001).

Wells, "Additivity of Mutational Effects in Proteins," *Biochemistry*, vol. 29, No. 37, pp. 8509-8517 (1990).

* cited by examiner

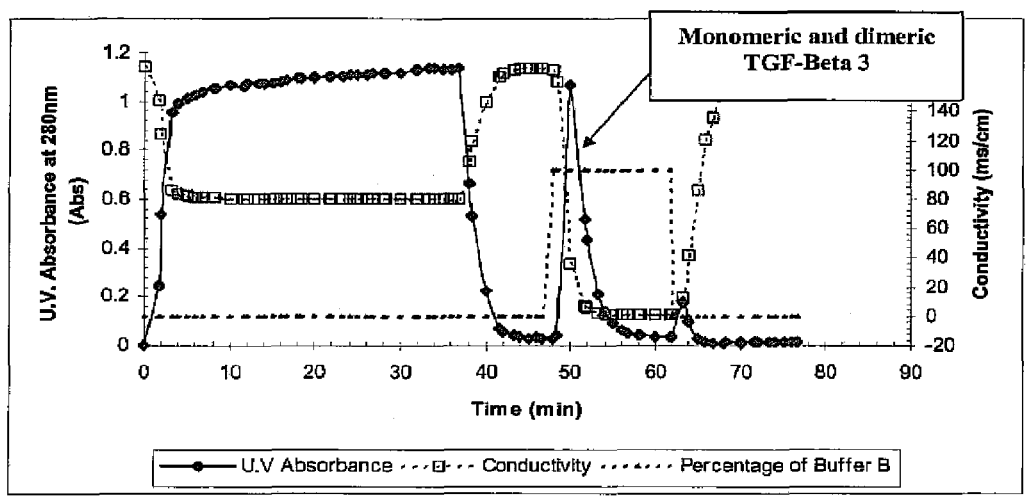
Figure 1. Chromatogram of TGF-Beta 3 'Wild-Type' on a Phenyl-Sepharose Column Figure 2. Chromatogram of TGF-Beta 3 'Wild-Type' Monomer and Dimer on UNO-S1 Column.
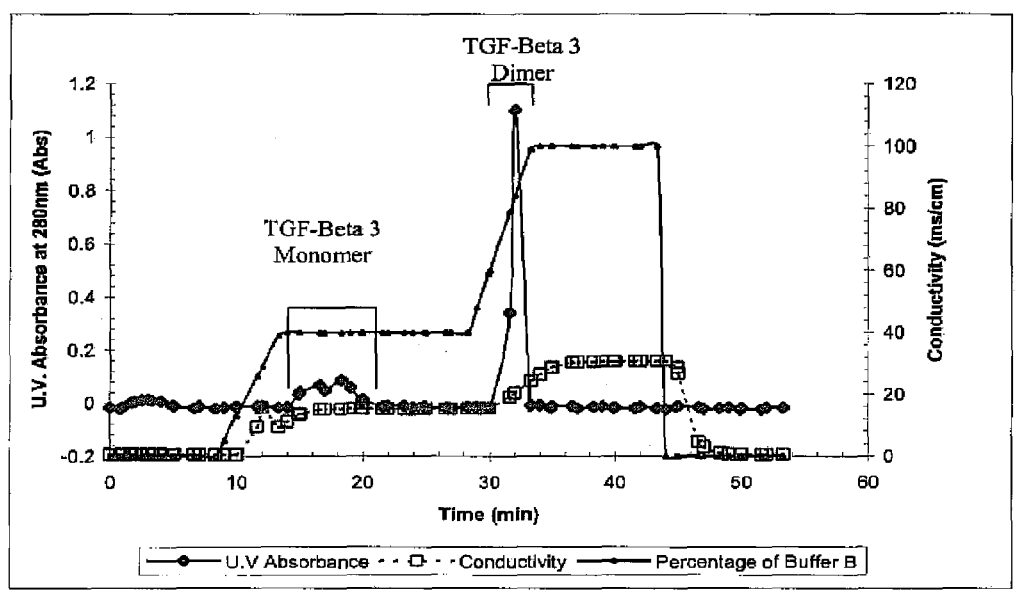

Figure 3. Comparison of TGF-Beta 3 Mutant Proteins and 'Wild-Type' TGF-Beta 3 by SDS-PAGE (Coomassie Blue stained)

| Track | Sample | Concentration loaded per track |
|---|---|---|
| 1 | TGF-Beta 3 'Wild-Type' | 3μg |
| 2 | Gly63-Ala | 3μg* |
| 3 | Gly63-Pro | 3μg* |
| 4 | Invitrogen Mark 12 molecular weight standards | 10μl |

* The buffer exchange of Gly63-Ala and Gly63-Pro mutant proteins resulted in some sample loss therefore the actual concentration added to the gel will be less than the 3μg stated.

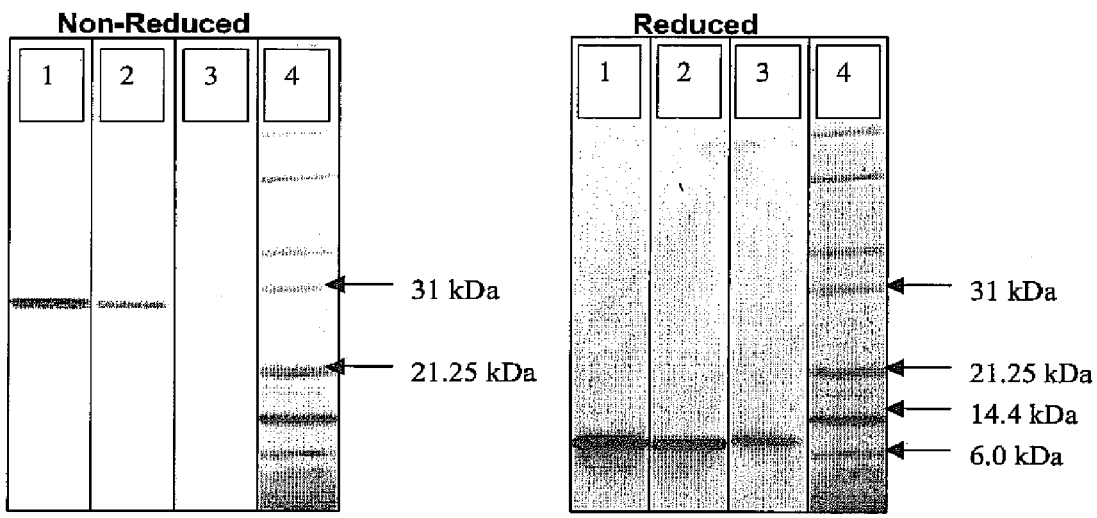

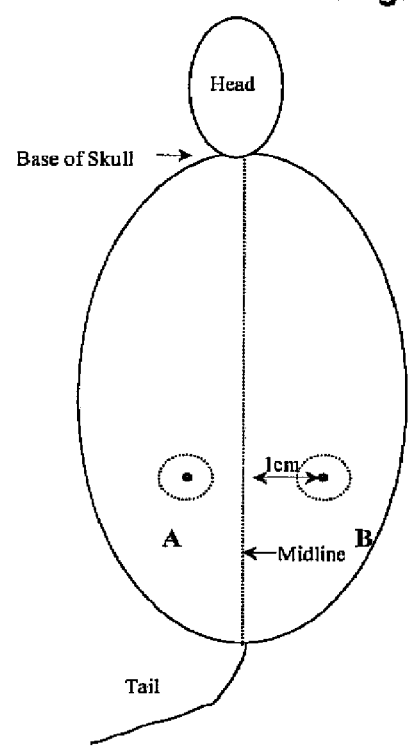
Figure 4. Template for Excisonal Wounding.

Figure 5. Day 3 Average Macroscore for Incisional wounds (A and B) treated with TGF-Beta 3 Wild-type' and Mutant proteins.
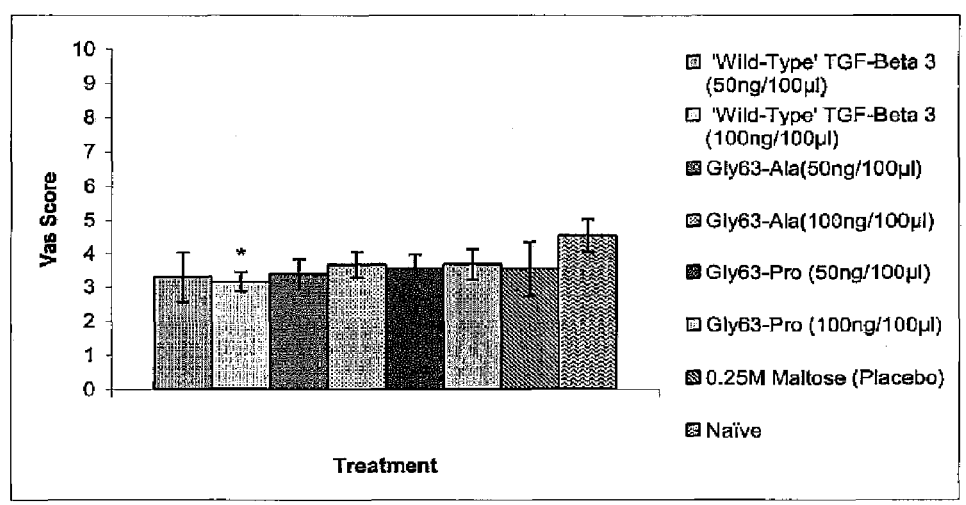
\* Significantly increased healing compared to naïve wounds ($p<0.05$).

Figure 6. Day 3 Microscopic Average Wound Width for Excisional wounds (C and D) Treated with 'Wild-type' and Mutant TGF-Beta 3 proteins.
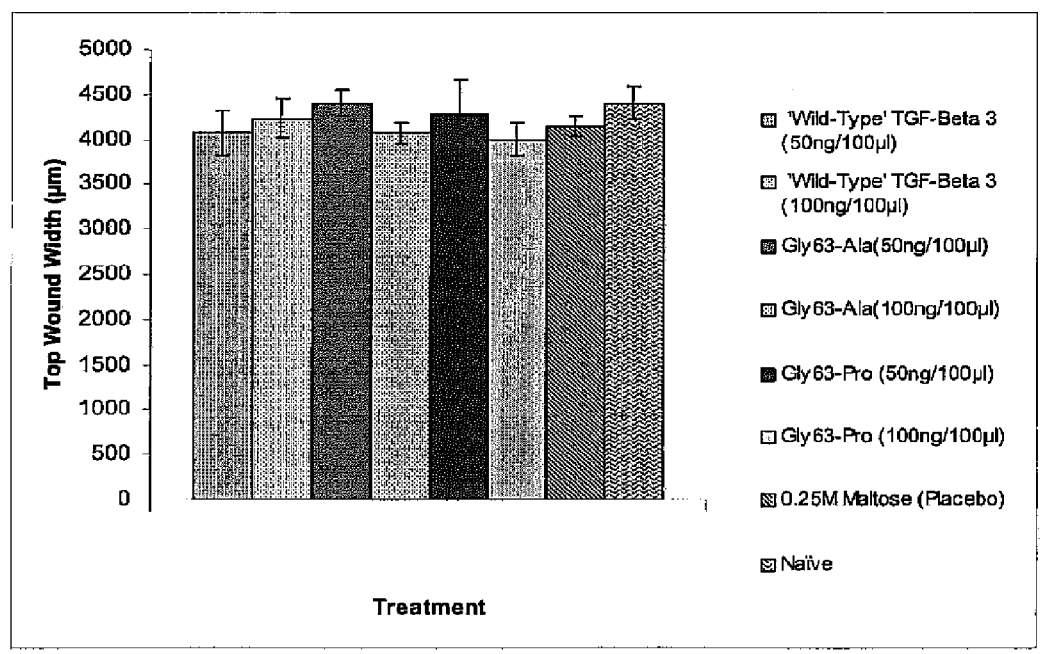

Figure 7. Template for Incisional Wounding.
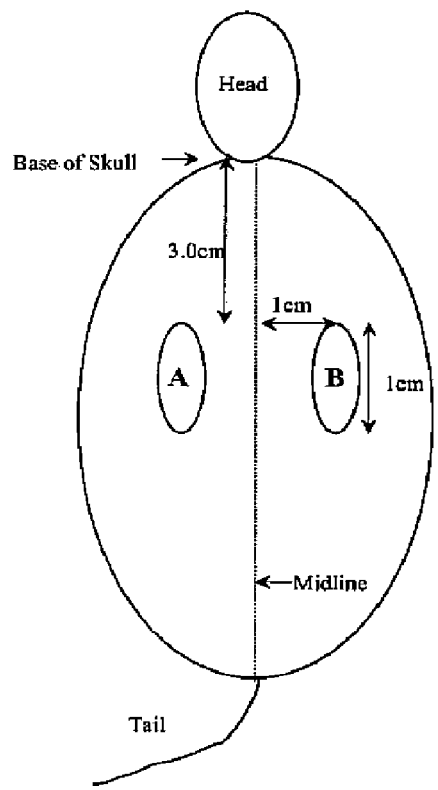

Figure 8. Day 70 Average Macroscore for Incisional wounds (A and B) treated with 'Wild-type' and Mutant TGF-Beta 3 proteins.
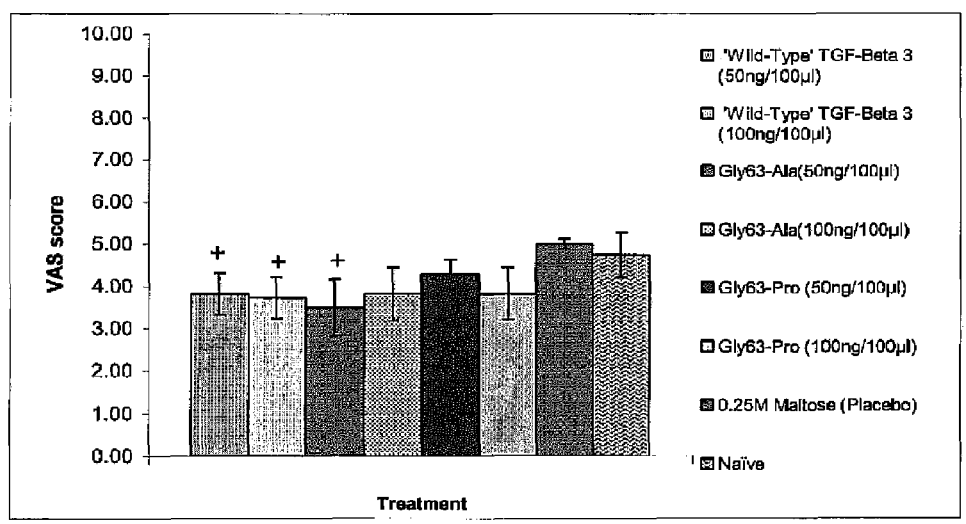
+ Significantly decreased scarring compared to placebo treated wounds (p<0.05)

Figure 9A. Representative Macroscopic Scar Images (70 days Post wounding)
'Wild-Type' TGF-Beta 3
(50ng/100µL)
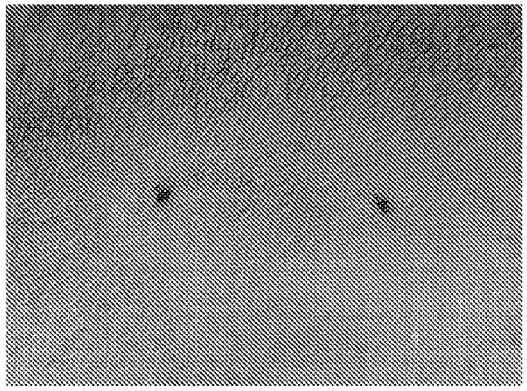
'Wild-Type' TGF-Beta 3
(100ng/100µL)
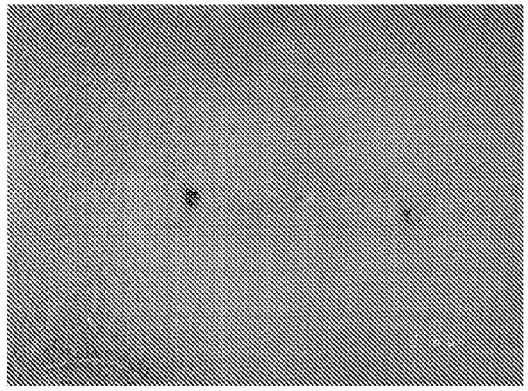
Gly63-Ala TGF-Beta 3
(50ng/100µL)
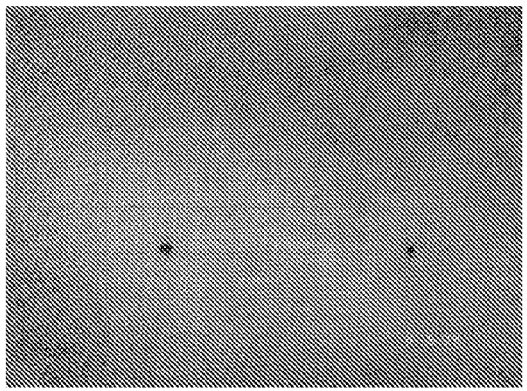
Gly63-Ala TGF-Beta 3
(100ng/100µL)
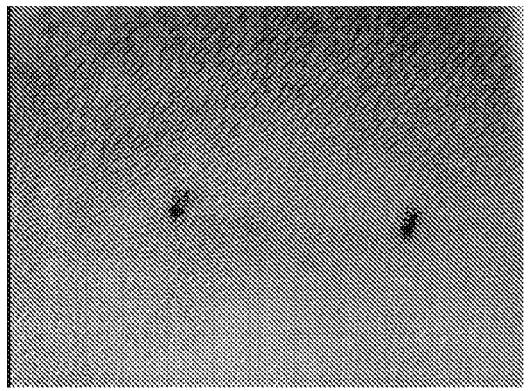

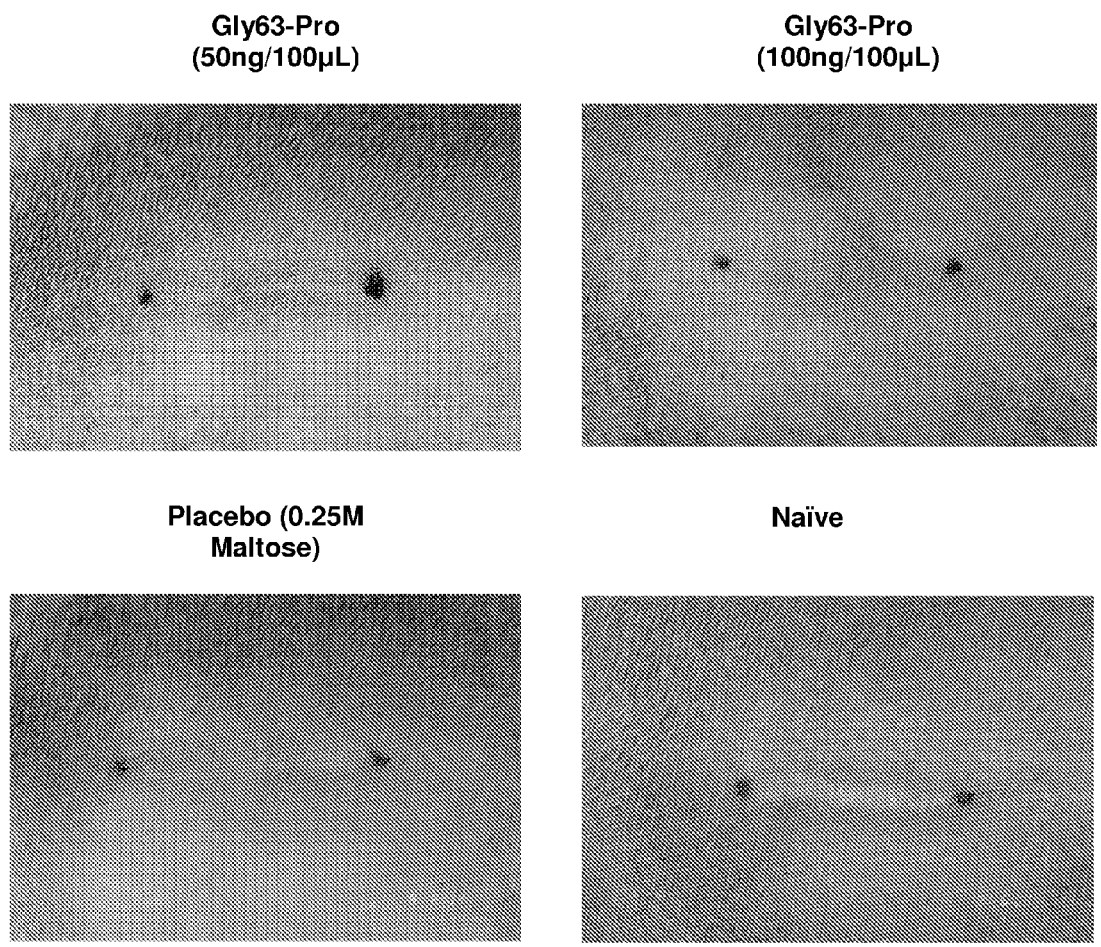
Figure 9B. Representative Macroscopic Scar Images (70 days Post wounding)

Figure 10. Day 70 Average Macroscore for Incisional wounds (A and B) treated with 'Wild-type' and Mutant TGF-Beta 3 proteins.
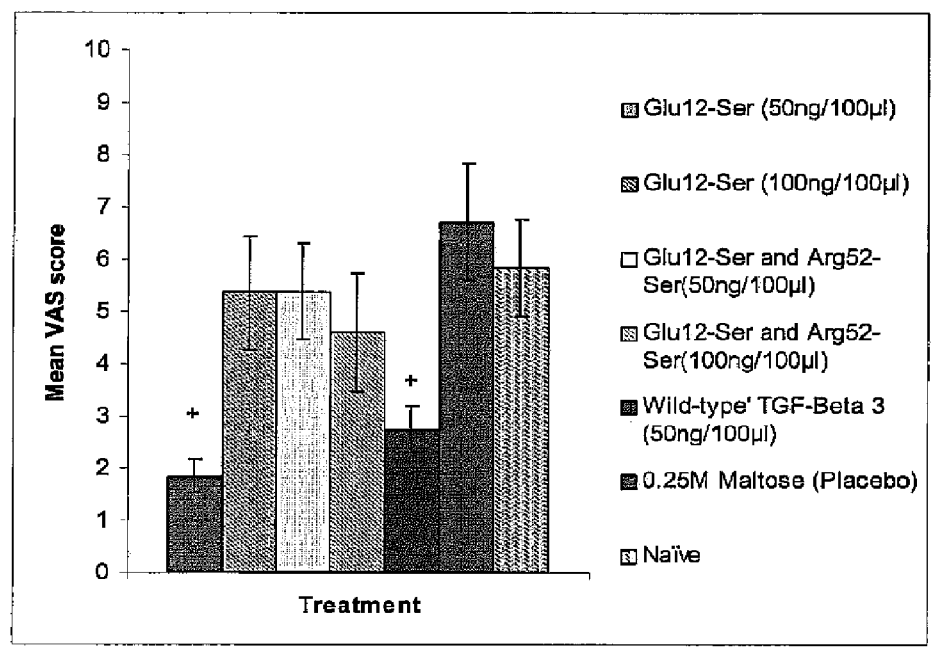
+ Significantly decreased scarring compared to placebo treated wounds ($p<0.05$)

Figure 11A. Representative Macroscopic Scar Images (70 days Post wounding)
Glu12-Ser (50ng/100μL)
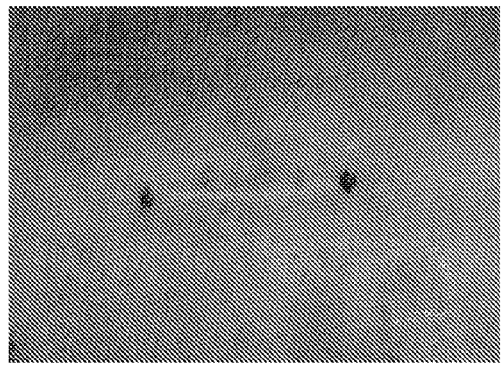
Glu12-Ser (100ng/100μL)
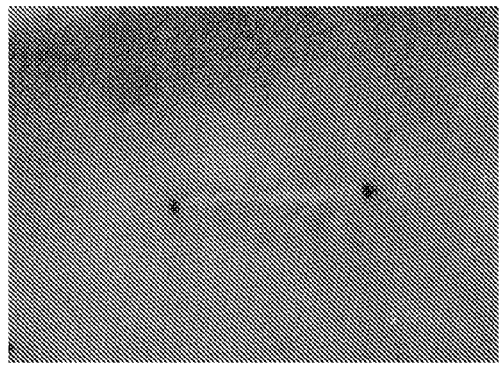
Glu12-Ser & Arg52-Ser
(50ng/100μL)
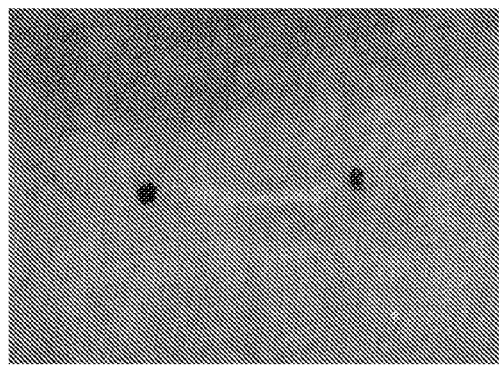
Glu12-Ser & Arg52-Ser
(100ng/100μL)
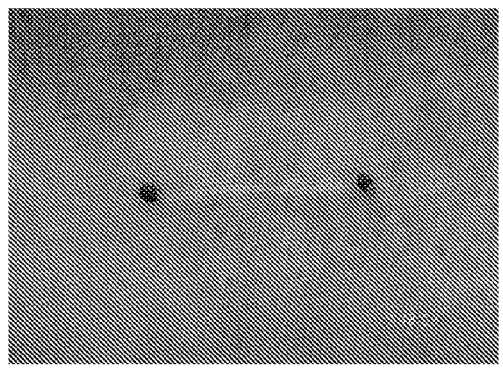

Figure 11B. Representative Macroscopic Scar Images (70 days Post wounding)
Wild-Type TGF-Beta 3(50ng/100μL)
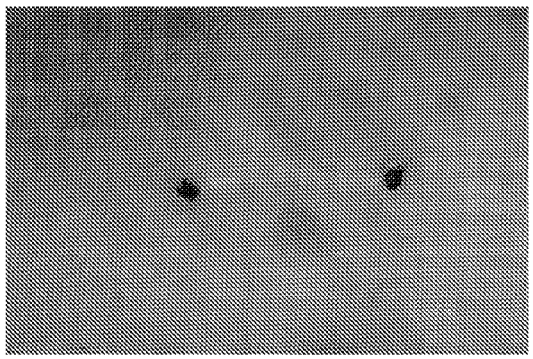
Placebo (0.25M Maltose) Control
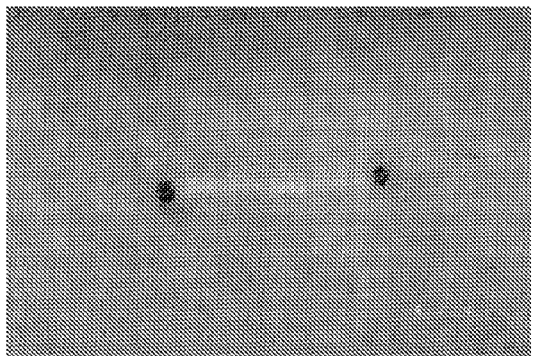
Naïve (Control)
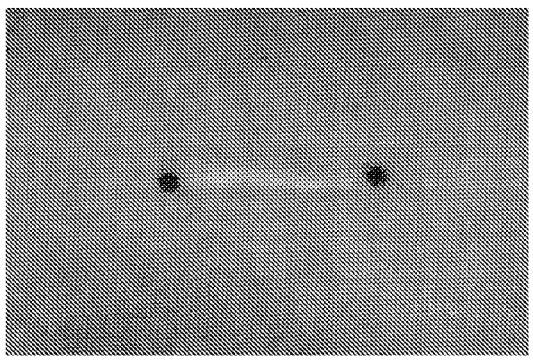

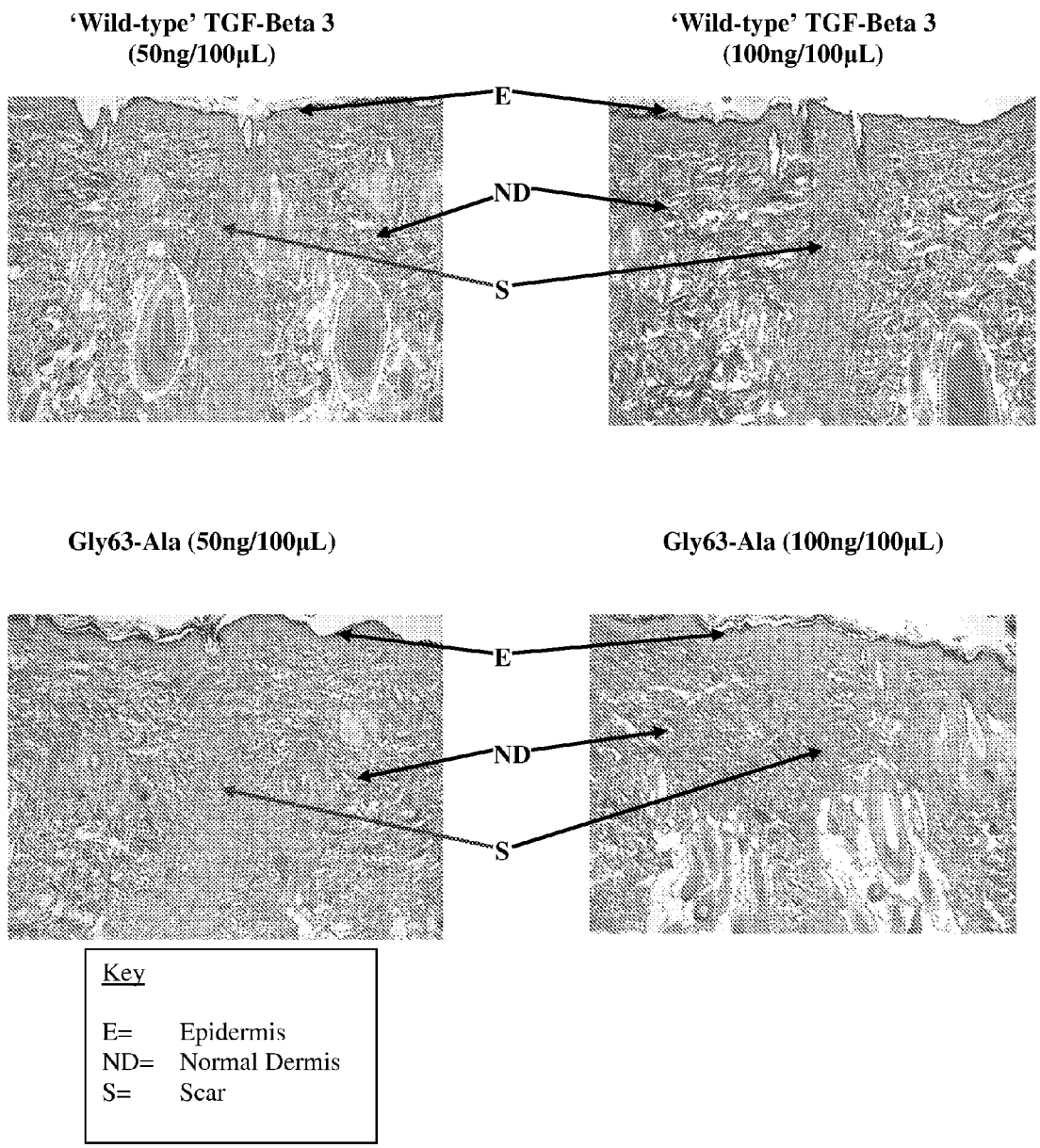
Figure 12A. Representative Microscopic Scar Images of Wounds Treated with 'Wild-type' TGF-Beta 3, Gly63-Pro and Gly63-Ala Mutant Proteins (70 days Post-Wounding).

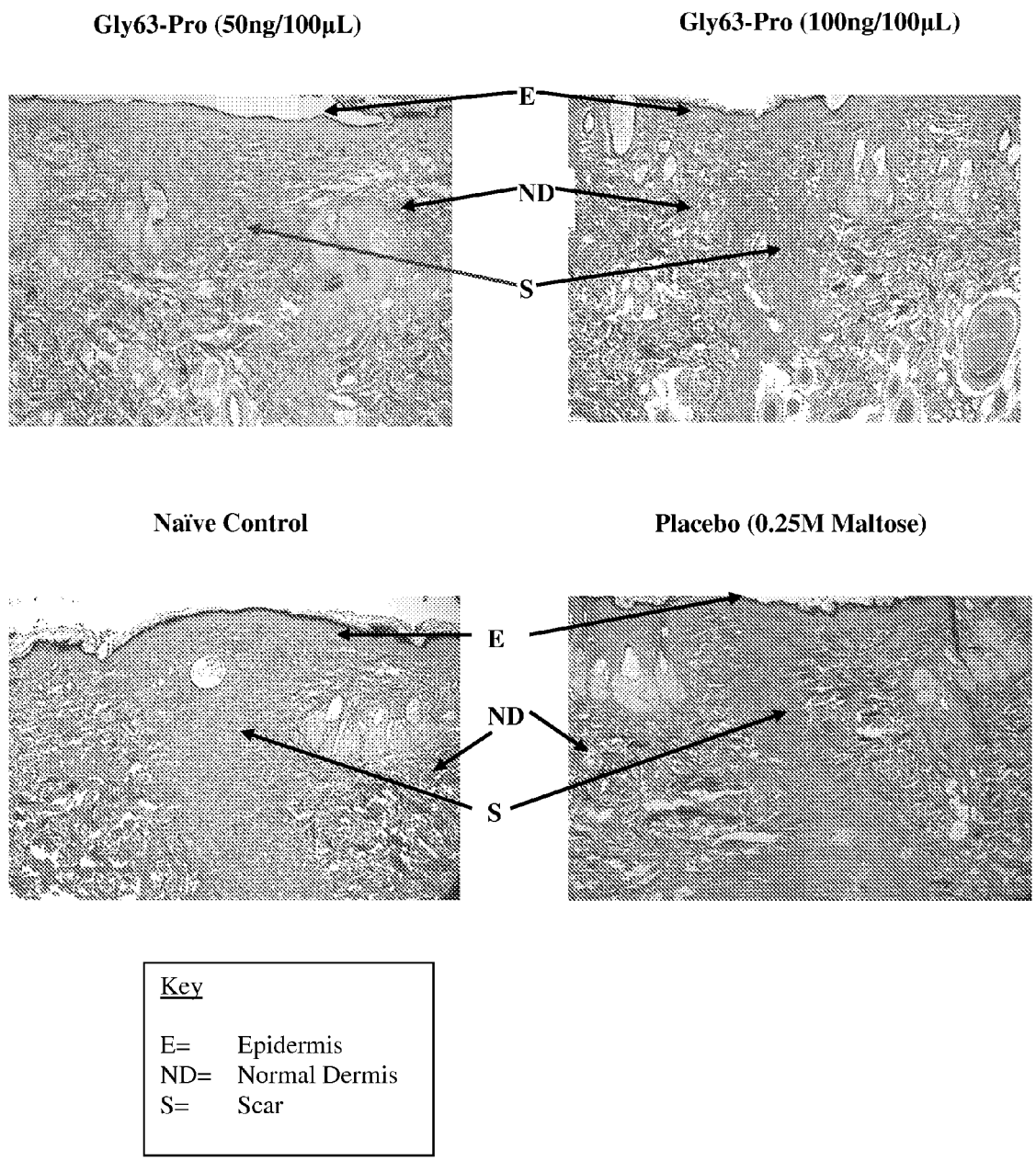
Figure 12B. Representative Microscopic Scar Images of Wounds Treated with 'Wild-type' TGF-Beta 3, Gly63-Pro and Gly63-Ala Mutant Proteins (70 days Post-Wounding)

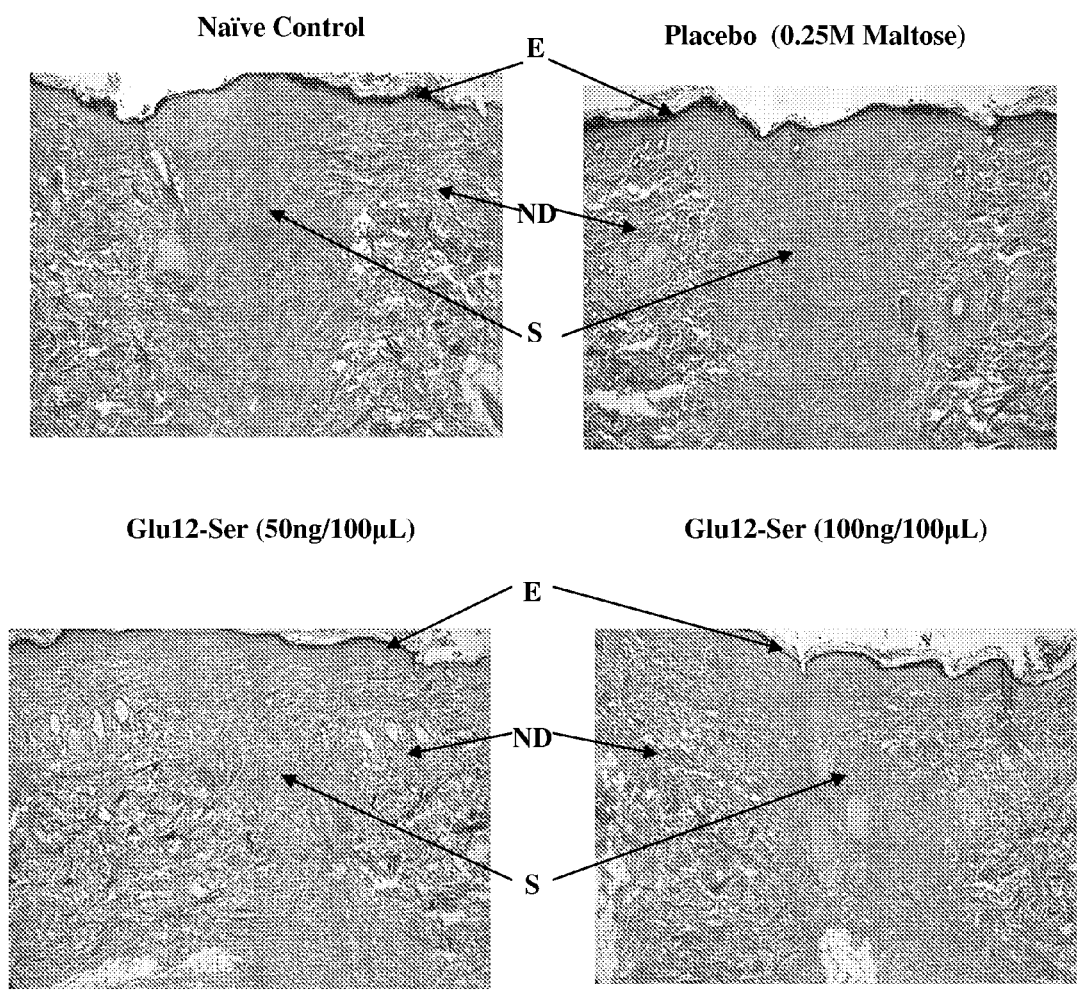
Figure 13A. Representative Microscopic Scar Images of Wounds Treated with Glu12-Ser and Double Serine mutant (Glu12-Ser and Arg 52-Ser) after 70 days Post-Wounding).

Figure 13B. Representative Microscopic Scar Images of Wounds Treated with Glu12-Ser and Double Serine mutant (Glu12-Ser and Arg 52-Ser) after 70 days Post-Wounding)
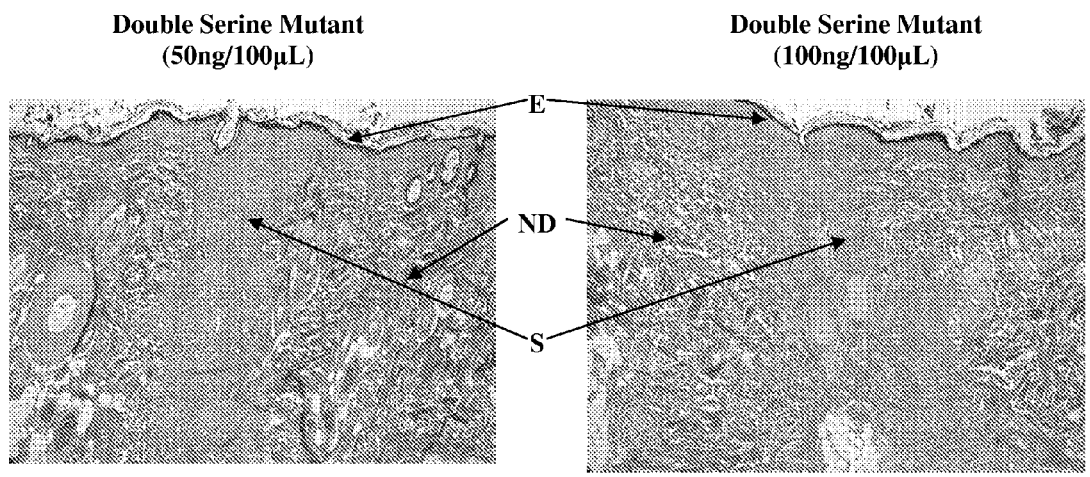
Key
E= Epidermis
ND= Normal Dermis
S= Scar

SEQUENCE LISTING

<160> NUMBER OF SEQ ID NOS: 16

<210> SEQ ID NO 1
<211> LENGTH: 112
<212> TYPE: PRT
<213> ORGANISM: Homo sapiens

<400> SEQUENCE: 1

```
Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Trp Lys Trp
            20                  25                  30

Val His Glu Pro Lys Gly Tyr Tyr Ala Asn Phe Cys Ser Gly Pro Cys
        35                  40                  45
```

```
Pro Tyr Leu Arg Ser Ala Asp Thr Thr His Ser Thr Val Leu Gly Leu
    50                  55                  60

Tyr Asn Thr Leu Asn Pro Glu Ala Ser Ala Ser Pro Cys Cys Val Pro
 65                  70                  75                  80

Gln Asp Leu Glu Pro Leu Thr Ile Leu Tyr Tyr Val Gly Arg Thr Pro
                 85                  90                  95

Lys Val Glu Gln Leu Ser Asn Met Val Val Lys Ser Cys Lys Cys Ser
            100                 105                 110

<210> SEQ ID NO 2
<211> LENGTH: 336
<212> TYPE: DNA
<213> ORGANISM: Homo sapiens

<400> SEQUENCE: 2
gctttggaca ccaattactg cttccgcaac ttggaggaga actgctgtgt gcgccccctc      60
tacattgact ccgacagga tctgggctgg aagtgggtcc atgaacctaa gggctactat     120
gccaacttct gctcaggccc ttgcccatac ctccgcagtg cagacacaac ccacagcacg     180
gtgctgggac tgtacaacac tctgaaccct gaagcatctg cctcgccttg ctgcgtgccc     240
caggacctgg agcccctgac catcctgtac tatgttggga ggaccccaa agtggagcag     300 ctctccaaca tggtggtgaa gtcttgtaaa tgtagc                                336

<210> SEQ ID NO 3
<211> LENGTH: 112
<212> TYPE: PRT
<213> ORGANISM: Artificial
<220> FEATURE:
<223> OTHER INFORMATION: Mutant TGF-beta 3 "Gly63-Ala"

<400> SEQUENCE: 3

Ala Leu Asp Thr Asn Tyr Cys Phe Arg Asn caggacctgg agcccctgac catcctgtac tatgttggga ggaccccccaa agtggagcag    300 ctctccaaca tggtggtgaa gtcttgtaaa tgtagc    336

<210> SEQ ID NO 5
<211> LENGTH: 112
<212> TYPE: PRT
<213> ORGANISM: Artificial
<220> FEATURE:
<223> OTHER INFORMATION: Mutant TGF-beta 3 "Gly63-Pro"

<400> SEQUENCE: 5

Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Trp Lys Trp
            20                  25                  30

Val His Glu Pro Lys Gly Tyr Tyr Ala Asn Phe Cys Ser Gly Pro Cys
        35                  40                  45

Pro Tyr Leu Arg Ser Ala Asp Thr Thr His Ser Thr Val Leu Pro Leu
    50                  55                  60

Tyr Asn Thr Leu Asn Pro Glu Ala Ser Ala Ser Pro Cys Cys Val Pro
65                  70                  75                  80

Gln Asp Leu Glu Pro Leu Thr Ile Leu Tyr Tyr Val Gly Arg Thr Pro
                85                  90                  95

Lys Val Glu Gln Leu Ser Asn Met Val Val Lys Ser Cys Lys Cys Ser
            100                 105                 110

<210> SEQ ID NO 6
<211> LENGTH: 336
<212> TYPE: DNA
<213> ORGANISM: Artificial
<220> FEATURE:
<223> OTHER INFORMATION: DNA encoding Gly63-Pro mutant

<400> SEQUENCE: 6
gctttggaca ccaattactg cttccgcaac ttggaggaga actgctgtgt gcgccccctc    60
tacattgact ccgacagga tctgggctgg aagtgggtcc atgaacctaa gggctactat    120
gccaacttct gctcaggccc ttgcccatac ctccgcagtg cagacacaac ccacagcacg    180
gtgctgccac tgtacaacac tctgaaccct gaagcatctg cctcgccttg ctgcgtgccc    240
caggacctgg agcccctgac catcctgtac tatgttggga ggaccccccaa agtggagcag    300 ctctccaaca tggtggtgaa gtcttgtaaa tgtagc    336

<210> SEQ ID NO 7
<211> LENGTH: 112
<212> TYPE: PRT
<213> ORGANISM: Artificial
<220> FEATURE:
<223> OTHER INFORMATION: Mutant TGF-beta 3 "Glu12-Ser"

<400> SEQUENCE: 7

Ala Leu Asp Thr Asn Tyr Cys Phe Arg Asn Leu Ser Glu Asn Cys Cys
1               5                   10                  15

Val Arg Pro Leu Tyr Ile Asp Phe Arg Gln Asp Leu Gly Trp Lys Trp
            20                  25                  30

Val His Glu Pro Lys Gly Tyr Tyr Ala Asn Phe Cys Ser Gly Pro Cys
        35                  40                  45

Pro Tyr Leu Arg Ser Ala Asp Thr Thr His Ser Thr Val Leu Gly Leu
    50                  55                  60

```
Tyr Asn Thr Leu Asn Pro Glu Ala Ser Ala Ser Pro Cys Cys Val Pro
 65                  70                  75                  80

Gln Asp Leu Glu Pro Leu Thr Ile Leu Tyr Tyr Val Gly Arg Thr Pro
                 85                  90                  95

Lys Val Glu Gln Leu Ser Asn Met Val Val Lys Ser Cys Lys Cys Ser
            100                 105                 110
```

<210> SEQ ID NO 8
<211> LENGTH: 336
<212> TYPE: DNA
<213> ORGANISM: Artificial
<220> FEATURE:
<223> OTHER INFORMATION: DNA encoding Glu12-Ser mutant

<400> SEQUENCE: 8

| | | | | | |
|---|---|---|---|---|---|
| gctttggaca | ccaattactg | cttccgcaac | ttgtcggaga | actgctgtgt | gcgccccctc | 60 |
| tacattgact | tccgacagga | tctgggctgg | aagtgggtcc | atgaacctaa | gggctactat | 120 |
| gccaacttct | gctcaggccc | ttgcccatac | ctccgcagtg | cagacacaac | ccacagcacg | 180 |
| gtgctgggac | tgtacaacac | tctgaaccct | gaagcatctg | cctcgccttg | ctgcgtgccc | 240 |
| caggacctgg | agcccctgac | catcctgtac | tatgttggga | ggacccccaa | agtggagcag | 300 |
| ctctccaaca | tggtggtgaa | gtcttgtaaa | tgtagc | | | 336 |

<210> SEQ ID NO 9
<211> LENGTH: 112
<212> TYPE: PRT
<213> ORGANISM: Artificial
<220> FEATURE:
<223> OTHER INFORMATION: Mutant TGF-beta 3 "Arg52-Ser"

<400> SEQUENCE: 9

```
Ala Leu Asp Thr Asn Tyr Cys Phe Arg Asn Leu Glu Glu Asn Cys Cys
  1               5                  10                  15

Val Arg Pro Leu Tyr Ile Asp Phe Arg Gln Asp Leu Gly Trp Lys Trp
             20                  25                  30

Val His Glu Pro Lys Gly Tyr Tyr Ala Asn Phe Cys Ser Gly Pro Cys
         35                  40                  45

Pro Tyr Leu Ser Ser Ala Asp Thr Thr His Ser Thr Val Leu Gly Leu
     50                  55                  60

Tyr Asn Thr Leu Asn Pro Glu Ala Ser Ala Ser Pro Cys Cys Val Pro
 65                  70                  75                  80

Gln Asp Leu Glu Pro Leu Thr Ile Leu Tyr Tyr Val Gly Arg Thr Pro
                 85                  90                  95

Lys Val Glu Gln Leu Ser Asn Met Val Val Lys Ser Cys Lys Cys Ser
            100                 105                 110
```

<210> SEQ ID NO 10
<211> LENGTH: 336
<212> TYPE: DNA
<213> ORGANISM: Artificial
<220> FEATURE:
<223> OTHER INFORMATION: DNA encoding Arg52-Ser mutant

<400> SEQUENCE: 10

| | | | | | |
|---|---|---|---|---|---|
| gctttggaca | ccaattactg | cttccgcaac | ttggaggaga | actgctgtgt | gcgccccctc | 60 |
| tacattgact | tccgacagga | tctgggctgg | aagtgggtcc | atgaacctaa | gggctactat | 120 |
| gccaacttct | gctcaggccc | ttgcccatac | ctcagcagtg | cagacacaac | ccacagcacg | 180 |
| gtgctgggac | tgtacaacac | tctgaaccct | gaagcatctg | cctcgccttg | ctgcgtgccc | 240 |

```
caggacctgg agcccctgac catcctgtac tatgttggga ggaccccccaa agtggagcag    300 ctctccaaca tggtggtgaa gtcttgtaaa tgtagc                              336
```

<210> SEQ ID NO 11
<211> LENGTH: 112
<212> TYPE: PRT
<213> ORGANISM: Artificial
<220> FEATURE:
<223> OTHER INFORMATION: Mutant TGF-beta 3 "Glu12-Ser/Arg52-Ser"

<400> SEQUENCE: 11

```
Ala Leu Asp Thr Asn Tyr Cys Phe Arg Asn Leu Ser Glu Asn Cys Cys
1               5                   10                  15

Val Arg Pro Leu Tyr Ile Asp Phe Arg Gln Asp Leu Gly Trp Lys Trp
            20                  25                  30

Val His Glu Pro Lys Gly Tyr Tyr Ala Asn Phe Cys Ser Gly Pro Cys
        35                  40                  45

Pro Tyr Leu Ser Ser Ala Asp Thr Thr His Ser Thr Val Leu Gly Leu
    50                  55                  60

Tyr Asn Thr Leu Asn Pro Glu Ala Ser Ala Ser Pro Cys Cys Val Pro
65                  70                  75                  80

Gln Asp Leu Glu Pro Leu Thr Ile Leu Tyr Tyr Val Gly Arg Thr Pro
                85                  90                  95

Lys Val Glu Gln Leu Ser Asn Met Val Val Lys Ser Cys Lys Cys Ser
            100                 105                 110
```

<210> SEQ ID NO 12
<211> LENGTH: 336
<212> TYPE: DNA
<213> ORGANISM: Artificial
<220> FEATURE:
<223> OTHER INFORMATION: DNA encoding Glu12-Ser/Arg52-Ser mutant

<400> SEQUENCE: 12

```
gctttggaca ccaattactg cttccgcaac ttgtcggaga actgctgtgt gcgccccctc     60
tacattgact ccgacagga tctgggctgg aagtgggtcc atgaacctaa gggctactat    120
gccaacttct gctcaggccc ttgcccatac ctcagcagtg cagacacaac ccacagcacg    180
gtgctgggac tgtacaacac tctgaaccct gaagcatctg cctcgccttg ctgcgtgccc    240
caggacctgg agcccctgac catcctgtac tatgttggga ggaccccccaa agtggagcag    300 ctctccaaca tggtggtgaa gtcttgtaaa tgtagc                              336
```

<210> SEQ ID NO 13
<211> LENGTH: 35
<212> TYPE: DNA
<213> ORGANISM: Artificial
<220> FEATURE:
<223> OTHER INFORMATION: Sense primer

<400> SEQUENCE: 13

```
gatataccat ggctttggac accaattact actgc                                35
```

<210> SEQ ID NO 14
<211> LENGTH: 37
<212> TYPE: DNA
<213> ORGANISM: Artificial
<220> FEATURE:
<223> OTHER INFORMATION: Sense primer

<400> SEQUENCE: 14

```
cagccggatc cggtcgactc agctacattt acaagac                              37
```

```
<210> SEQ ID NO 15
<211> LENGTH: 20
<212> TYPE: DNA
<213> ORGANISM: Artificial
<220> FEATURE:
<223> OTHER INFORMATION: T7 promoter primer

<400> SEQUENCE: 15
taatacgact cactataggg                                                 20

<210> SEQ ID NO 16
<211> LENGTH: 19
<212> TYPE: DNA
<213> ORGANISM: Artificial
<220> FEATURE:
<223> OTHER INFORMATION: T7 terminator primer

<400> SEQUENCE: 16
gctagttatt gctcagcgg                                                  19
```

TGF-β3 MUTANTS

CROSS-REFERENCE TO RELATED APPLICATIONS

This application is the national stage of International (PCT) Patent Application Ser. No. PCT/GB2007/000833, filed Mar. 12, 2007, which claims priority to Great Britain Patent Application No. 0604938.1, filed Mar. 11, 2006; the contents of each application is incorporated herein by reference in its entirety.

The present invention relates to proteins derived from TGF-β3, to biologically active fragments of such proteins, and also to nucleic acids encoding said proteins. The invention also provides derivatives of such proteins or biologically active fragments. The invention further provides medicaments comprising the proteins, fragments, derivatives or nucleic acids of the invention, as well as methods of treatment utilising the proteins, fragments, derivatives or nucleic acids.

The transforming growth factor betas (TGF-βs) are part of a superfamily of growth factors involved in the regulation of many cellular processes including proliferation, migration, apoptosis, adhesion, differentiation, inflammation, immunosuppression and expression of extracellular proteins.

There are three mammalian isoforms of TGF-β, termed TGF-β1, TG-β2 and TGF-β3. TGF-βs are produced by a wide range of cell types including epithelial, endothelial, hematopoietic, neuronal, and connective tissue cells.

The TGF-βs have utility in many different therapeutic contexts, and the TGF-β3 isoform in particular has many advantageous therapeutic uses. As a result of the therapeutic potential of TGF-β3s there is much interest in its pharmaceutical applications. The amino acid sequence of full-length wild type TGF-β3 is set out in Sequence ID No. 1, and cDNA encoding this TGF-β3 is set out in Sequence ID No. 2.

TGF-β3 is known to play a crucial role in the regulation of the wound healing response. The activity of TGF-β3 may influence the rate of wound healing as well as the extent of scarring that occurs as a result of healing.

TGF-β3 may also be used in the treatment of fibrotic disorders, pulmonary fibrosis, liver cirrhosis, scleroderma, angiogenesis disorders, restenosis, adhesions, endometriosis, ischemic disease, bone and cartilage induction, in vitro fertilisation, oral mucositis, renal disease, prevention, reduction or inhibition of scarring, enhancement of neuronal reconnection in the peripheral and central nervous system, preventing, reducing or inhibiting complications of eye surgery (such as LASIK or PRK surgery) or scarring at the back of the eye (such as proliferative vitreoretinopathy).

The therapeutic uses to which TGF-β3 lends itself have established a well-recognised need for sources of biologically active TGF-β3 proteins, and numerous attempts have been made to produce this valuable protein by recombinant methods. However, existing processes for the production of TGF-β3 are severely limited due to the necessity for refolding of the complex protein in order to achieve biologically active molecules.

TGF-βs naturally exist as homodimeric proteins comprised of two 112 amino acid subunits. Each of these TGF-β3 subunits contains an alpha-helix forming domain between the 58$^{th}$ and 67$^{th}$ residues of the active peptide fragment. In addition to the alpha-helix between residues 58 and 67, each TGF-β3 subunit also contains a number of intra-subunit linkages including salt bridges and disulphide bonds.

TGF-β3 is secreted as a 100-kDa latent inactive precursor molecules (LTGF-β3). The LTGF-β3 molecule consists of:

i) C-terminal 25kDa dimer signal peptide (active fragment); and
ii) latent-associated peptide (LAP).

LTGF-β is activated by dissociation of LAP from the active fragment. Cleavage of LTGF-β may be mediated by the action of enzymes such as endopeptidases like furin, plasmin and thrombin or by acidification of the pericellar space. The active TGF-β dimeric fragment is stabilized by hydrophobic and ionic interactions, which are further strengthened by an inter-subunit disulfide bridge. Each monomer comprises several extended beta strands interlocked by three of the four intra-disulfide bonds and forms a tight structure known as the "cysteine knot".

Due to the complexity of biologically active TGF-β3 molecules (which are, as set out above, homodimeric proteins with 8 intra-chain disulfide bonds and one inter-chain disulfide bond) they were originally expressed in eukaryotic organisms. However, the relatively low expression levels that may be achieved using eukaryotic expression systems, in combination with the high costs of such processes, mean that the use of microbial hosts was investigated in order to attempt to improve the commercial efficiency of TGF-β3 production.

The disadvantage of using microbial hosts such as E. coli to express recombinant molecules, such as TGF-β3, that contain multiple disulfide bonds is that the proteins produced are normally incorrectly folded, and often form insoluble inclusion bodies. These inclusion bodies require solubilisation followed by renaturation to allow the protein to re-fold into its native biological active conformation. To effectively renature TGF-β3 homodimer, covalent disulfide bonds in the correct orientation need to be regenerated. The likelihood of forming the correct TGF-β3 homodimer from the process of random disulfide bond formation is low given that there are nine disulfide bonds, allowing 34,459,245 possible disulfide bond combinations. It is therefore not surprising that the re-folding of recombinantly produced TGF-β3 can severely impact on its manufacture, since this refolding may take up to 144 hours, and typically only achieves re-folding efficiencies of in the region of 20%.

It is an aim of the present invention to obviate or mitigate some of the problems associated with the prior art. It is an aim of certain aspects of the present invention to provide TGF-β3s (or fragments or derivatives thereof) that have improved refolding efficiency as compared to wild type TGF-β3. It is another aim of certain aspects of the invention to provide agents other than wild type TGF-β3 that have TGF-β3 activity. Such agents may provide valuable alternatives to naturally occurring TGF-β3.

In a first aspect of the present invention there is provided a TGF-β3, or a fragment or derivative thereof, wherein the alpha-helix-forming domain between amino acid residues 58 and 67 of full-length wild type TGF-β3 comprises at least one alpha-helix-stabilising substitution. The invention also provides a nucleic acid encoding a TGF-β3, or fragment or derivative thereof, in accordance with the first aspect of the invention.

The inventors have surprisingly found that the new TGF-β3s disclosed in the first aspect of the invention share the same biological activity as naturally occurring TGF-β3, and have much improved protein refolding efficiency when compared to wild-type TGF-β3. This increased protein refolding efficiency constitutes a marked and important advantage since it both simplifies the refolding conditions that may be used to produce biologically active TGF-β3s and also greatly increases the yield of such proteins (or fragments or derivatives of such proteins) that may be produced using prokaryotic protein expression systems.

Without wishing to be bound by any hypothesis, the inventors believe that the introduction of alpha-helix-stabilising substitutions into the alpha-helix-forming domain advantageously decreases the flexibility of the alpha-helix formed by this domain. This decreased flexibility helps to promote proper refolding of TGF-β3s in accordance with the first aspect of the invention to produce biologically active proteins (or fragments or derivatives thereof). The decreased flexibility imparted by stabilisation of the alpha-helix through alpha-helix-stabilising substitutions is sufficient to increase yields of correctly refolded TGF-β3 (particularly refolded dimeric TGF-β3), but, surprisingly, the inventors have found that such substitutions do not alter the biological activity of TGF-β3s in accordance with the first aspect of the invention, nor do they detract from their biological and therapeutic effectiveness.

Except for where the context requires otherwise, the numbering of amino acid residues in the present specification is based upon the amino acid sequence of the active peptide portions of TGF-β3s. For example, references to "full-length wild type TGF-β3" should generally be taken to refer to the amino acid sequence of the active peptide shown in Sequence ID No. 1, and references to the alpha-helix-forming domain between amino acid residues 58 and 67 are to be construed accordingly.

An alpha-helix-stabilising substitution may preferably comprise a substitution of the Glycine residue at position 63 of full-length wild type TGF-β3. However, suitable substitutions may additionally or alternatively comprise substitutions of, for example, one or both of the Threonines at positions 60 or 67 of full-length wild type TGF-β3, or of the Asparagine at position 66 of full-length wild type TGF-β3. It may be preferred that alpha-helix-stabilising substitutions for use in accordance with the invention do not comprise substitution of Valine 61.

An "alpha-helix-stabilising substitution" in accordance with the present invention should be understood to be a substitution in which a given amino acid residue present in wild type TGF-β3 is substituted by a replacement residue having a greater propensity for alpha-helix formation. Thus the replacement amino acid residue introduced in an alpha-helix-stabilising substitution need not necessarily be one which is itself predisposed to stable integration into alpha-helices, but need only have a greater propensity for stable integration than does the amino acid substituted. However, it may generally be preferred that a replacement amino acid introduced as part of an alpha-helix-stabilising substitution is an amino acid residue that does favour integration into an alpha-helix.

The inventors have found that preferred replacement amino acid residues that may be introduced in alpha-helix-stabilising substitutions in accordance with the first aspect of the invention may be any one or combination of amino acids selected from the group comprising: Alanine, Serine, Threonine, Valine, Leucine, Isoleucine; Methionine and Phenylalanine. These preferred replacement amino acid residues are all considered to be suitable for use in alpha-helix-stabilising substitutions of the Glycine residue at position 63 of full-length wild type TGF-β3. That said, replacement amino acid residues selected from this group may be substituted at any position in the alpha-helix-forming domain between amino acid residues 58 and 67 at which they may provide an alpha-helix-stabilising substitution.

Although the amino acid residues listed above represent preferred residues for use in alpha-helix-stabilising substitutions, it will be appreciated that there are a number of alternative qualitative and quantitative systems by which the propensity of an amino acid residue to contribute to alpha-helix formation (and thereby the suitability of the residue for use in a alpha-helix-stabilising substitution) may be measured, and that suitable amino acid residues for use in alpha-helix-stabilising substitutions may be selected with reference to any of these systems in combination with knowledge of the sequence of TGF-β3.

By way of example, a qualitative system described by Chou and Fasman identifies five different classifications of amino acid residues based on their propensity for alpha-helix formation. In order, these are:
Strong helix formers;
Weak helix formers;
Indifferent forms;
Weak helix breakers; and
Strong helix breakers.

For the purposes of the present specification, the amino acid residues Glutamic acid, Histidine, Tryptophan, Lysine, Alanine, Methionine, Valine, Isoleucine, Leucine, Glutamine and Phenylalanine may be considered to be helix formers, with Glutamine, Methionine, Alanine and Leucine constituting strong helix formers. In contrast, Asparagine, Glycine and Proline may be considered to constitute helix breakers, with Glycine and Proline being strong helix breakers.

Thus, if the propensity for alpha-helix formation is assessed with reference to this qualitative scale it will be recognised that, although an alpha-helix-stabilising substitution may preferably be one in which an amino acid residue is replaced with a helix former, suitable alpha-helix-stabilising substitutions may alternatively make use of indifferent forms or even helix breakers depending on the nature of the amino acid residue that is to be replaced. For example, in the case that in indifferent form amino acid residue is to be the subject of an alpha-helix-stabilising substitution, a suitable replacement amino acid residue may be a strong helix former or a weak helix former. In the case that a strong helix breaker is to be the subject of an alpha-helix-stabilising substitution, the replacement amino acid residue may be a strong helix former, a weak helix former, an indifferent form amino acid or a weak helix breaker.

Accordingly, an alpha-helix-stabilising substitution in accordance with the present invention may comprise the substitution of a strong helix breaker with a weak helix breaker, or an indifferent form amino acid residue, or a weak helix former, or a strong helix former. Alternatively or additionally, a suitable alpha-helix-stabilising substitution may comprise the substitution of a weak helix breaker with an indifferent form, a weak helix former, or a strong helix former. Alternatively or additionally, a suitable alpha-helix-stabilising substitution may comprise the substitution of an indifferent form amino acid with a weak helix former or a strong helix former. Alternatively or additionally, a suitable alpha-helix-stabilising substitution may comprise the substitution of a weak helix former with a strong helix former.

An alternative assessment of the propensity of an amino acid residue for alpha-helix formation, and therefore its suitability to be utilised as part of an alpha-helix-stabilising substitution, may be based upon any of the number of quantitative scales known to those skilled in the art.

An example of such a quantitative scale that may be used in determining an amino acid residue's suitability for use in an alpha-helix-stabilising substitution is set out in Table 1. This table provides values, calibrated in kcal/mol, reflecting the propensity of amino acids to contribute to alpha-helix formation. A high value in Table 1 is associated with a low tendency to alpha-helix formation.

Thus, when the suitability of an amino acid residue for use in an alpha-helix-stabilising substitution as required by the first aspect of the invention is assessed using a quantitative scale, such as that set out in Table 1, a suitable alpha-helix-stabilising substitution is one in which an amino acid residue is substituted by a replacement amino acid residue that has a greater helix-forming propensity (indicated in Table 1 by a lower kcal/mol value) than the residue being replaced.

Suitable substitutions that may be utilised in accordance with the invention include those that introduce artificial replacement amino acids. Suitable examples of artificial amino acids that may be beneficially used to stabilise alpha-helices include amino acid residues having alkyl and hydroxyl side chains.

Alanine represents a particularly preferred replacement amino acid residue suitable for use in alpha-helix-stabilising substitutions. It is most preferred that a TGF-β3, or fragment or derivative thereof, in accordance with the first aspect of the invention comprises the replacement of Glycine at position 63 of full-length wild type TGF-β3 with alanine.

The amino acid sequence of a preferred TGF-β3 in accordance with the first aspect of the invention is set out in Sequence ID No. 3 (Gly-63Ala), and DNA encoding this TGF-β3 is set out in Sequence ID No. 4. Fragments or derivatives of the TGF-β3 of Sequence ID No. 3 containing the Alanine substitution at position 63 of full-length wild type TGF-β3 represent preferred TGF-β3 fragments or derivatives in accordance with the first aspect of the invention.

A suitable substitution may be one in which one or more amino acid residues located between 58 and 67 of full-length wild type TGF-β3 are replaced with one or more natural or artificial amino acid residues. By way of further clarification, suitable substitutions may involve the substitution of a single amino acid residue with one or more replacement residues, or the substitution of more than one amino acid residues with one or more replacement residues. A preferred substitution may be one in which the number of amino acid residues is conserved, i.e. one in which the number of amino acid residues substituted is the same as the number of replacement amino acid residues introduced.

It will further be appreciated that preferred amino acid residue (or residues) to be replaced may be selected with reference to the qualitative or quantitative scales discussed above. Thus a suitable amino acid to be the subject of an alpha-helix-stabilising substitution may be one classified as a helix breaker, or preferably a strong helix breaker, with reference to the qualitative scale discussed above. With reference to the quantitative scale set out in Table 1, a suitable amino acid to be the subject of an alpha-helix-stabilising may preferably be one with a helix propensity value greater than or equal to 0.50, more preferably with a helix propensity value greater than or equal to 0.60, and most preferably with a helix propensity value of 1.00.

The inventors believe that TGF-β3s, or biologically active fragments or derivatives thereof, in accordance with the first aspect of the invention may be used in all contexts in which it may be wished to make use of the biological activities of wild type TGF-β3. These particularly include, but are not limited to, therapeutic uses. In keeping with this therapeutic use the invention also provides the use of a TGF-β3, or a fragment or derivative thereof, in accordance with the first aspect of the invention as a medicament.

It will be appreciated that, although it may be preferred that a fragment or derivative of a TGF-β3 in accordance with the first aspect of the invention comprise the full-length alpha-helix-forming domain containing an alpha-helix-stabilising substitution, this need not necessarily be the case. A suitable fragment or derivative may comprise a truncated alpha-helix-forming domain as long as this truncated alpha-helix forming domain comprises at least one alpha-helix-stabilising substitution.

In a second aspect of the invention there is provide a TGF-β3, or a fragment or derivative thereof, wherein the Glycine residue at position 63 of full-length wild type TGF-β3 is replaced with Proline. The invention also provides a nucleic acid molecule encoding a TGF-β3, or a fragment or derivative thereof, in accordance with the second aspect of the invention.

The inventors have surprisingly found that proteins in accordance with the second aspect of the invention (or their fragments or derivatives) have biological activity comparable to that of wild type TGF-β3. This finding is unexpected, since it may be thought that the presence of Proline in a region of TGF-β3 normally associated with alpha-helix formation would interfere with the secondary structure of such proteins and thereby impair their biological function. Although the refolding efficiency of TGF-β3s in accordance with the second aspect of the invention is lower than that of wild type TGF-β3 the anticipated impairment of function surprisingly does not occur.

Thus proteins in accordance with the second aspect of the invention (or their fragments or derivatives) provide a valuable contribution to the art in that they expand the repertoire of compounds capable of exerting TGF-β3 activity that are available to the skilled person. Such compounds may, for example, be used in contexts in which it is desired to use TGF-β3 activity therapeutically.

The amino acid sequence of a preferred TGF-β3 in accordance with the second aspect of the invention is set out in Sequence ID No. 5 (Gly-63Pro), and DNA encoding this TGF-β3 is set out in Sequence ID No. 6. Fragments or derivatives of the TGF-β3 of Sequence ID No. 5 containing the proline substitution at position 63 of full-length wild type TGF-β3 represent preferred TGF-β3 fragments or derivatives in accordance with the second aspect of the invention.

Given that TGF-β3s, or fragments or derivatives thereof, in accordance with the second aspect of the invention may be used in contexts in which it is desired to utilise the therapeutic biological activity of wild type TGF-β3 it will be appreciated that that there is also provided the use of TGF-β3s, or fragments or derivatives thereof, in accordance with the second aspect of the invention as medicaments. The inventors believe that such medicaments may be used in all clinical contexts in which it is known to make use of the biological activity of TGF-β3.

In a third aspect of the invention there is provided a TGF-β3, or a fragment or derivative thereof, comprising a substitution of the glutamic acid residue at position 12 of full-length wild type TGF-β3 and/or the arginine residue at position 52 of full-length wild type TGF-β3. The invention also provides a nucleic acid molecule encoding a TGF-β3, or a fragment or derivative thereof, in accordance with the third aspect of the invention.

It will be appreciated that the third aspect of the invention thus encompasses TGF-β3s in which the Glutamic acid at position 12 of full-length wild type TGF-β3 is substituted but the arginine at position 52 of full-length wild type TGF-β3 is retained. The third aspect of the invention also encompasses TGF-β3s in which the Glutamic acid at position 12 of full-length wild type TGF-β3 is retained but the arginine at position 52 of full-length wild type TGF-β3 is substituted.

However, it is preferred that TGF-β3s in accordance with the third aspect of the invention comprise substitutions of both the Glutamic acid residue at position 12 of full-length wild type TGF-β3 and the arginine residue at position 52 of full-length wild type TGF-β3.

The inventors have surprisingly found that proteins in accordance with the third aspect of the invention also have biological activity comparable to that of wild type TGF-β3. This finding is unexpected, since the substitution of one or both of the Glutamic acid residue at position 12 of full-length wild type TGF-β3 and/or the Arginine residue at position 52 of full-length wild type TGF-β3 disrupts the formation of one of the intra-subunit salt bridges normally found in wild type TGF-β3. This failure to complete proper salt bridge formation may be expected to decrease the biological activity of TGF-β3s in accordance with the third aspect of the invention since the biological activity of proteins such as TGF-βs is generally believed to be dependent on their conformation.

Furthermore, the inventors have further found that TGF-β3s in accordance with the second aspect of the invention exhibit an efficiency of successful refolding of that is just as high as that observed for wild type TGF-β3. This finding is highly surprising, since it would be expected by those skilled in the art that the lack of intra-subunit salt bridge formation that must take place in TGF-β3s in accordance with the second aspect of the invention would deleteriously impact on the incidences of refolding and hence decrease the yield of biologically active TGF-β3.

Thus proteins in accordance with the third aspect of the invention serve to expand the repertoire of compounds capable of exerting TGF-β3 activity that are available to the skilled person. As noted above, that availability of such compounds is of important in contexts such as those in which it is desired to use TGF-β3 activity therapeutically.

The inventors have found that one or other of the Glutamic acid at position 12 of full-length wild type TGF-β3 or the Arginine at position 52 of full-length wild type TGF-β3 may be substituted by any one amino acid residue (or any combination of amino acid residues) selected from the group comprising Serine, Alanine, Threonine, Valine, Isoleucine, Methionine, Phenylalanine and Leucine.

It is preferred that Serine be used as a replacement amino acid residue in TGF-β3s, or fragments or derivatives thereof, in accordance with the third aspect of the invention. Serine may be used as a replacement for the Glutamic acid at position 12 of full-length wild type TGF-β3 or the Arginine at position 52 of full-length wild type TGF-β3. Most preferably serine is used to replace both the Glutamic acid at position 12 of full-length wild type TGF-β3 and the Arginine at position 52 of full-length wild type TGF-β3.

A first example of a preferred TGF-β3 in accordance with the third aspect of the invention is set out in Sequence ID No. 7. The invention encompasses biologically active fragments or derivatives of Sequence ID No. 7 comprising the Glu12-Ser substitution. cDNA encoding this preferred TGF-β3 is set out in Sequence ID No. 8.

A second example of a preferred TGF-β3 in accordance with the third aspect of the invention is set out in Sequence ID No. 9. Biologically active fragments or derivatives of Sequence ID No. 9 comprising the Arg52-Ser substitution also constitute preferred fragments or derivatives in accordance with the invention. cDNA encoding this preferred TGF-β3 is set out in Sequence ID No. 10.

A third example of a preferred TGF-β3 in accordance with the third aspect of the invention is set out in Sequence ID No. 11. Biologically active fragments or derivatives of Sequence ID No. 11 that comprise both the Glu12-Ser substitution and the Arg52-Ser substitution also constitute preferred fragments or derivatives in accordance with the invention. cDNA encoding this preferred TGF-β3 is set out in Sequence ID No. 12.

The inventors believe that TGF-β3s, or biologically active fragments or derivatives thereof, in accordance with the third aspect of the invention may be used in all contexts in which it may be wished to make use of the biological activities of wild type TGF-β3. These include, but are not limited to, therapeutic uses of TGF-β3. Accordingly the invention also provides the use of a TGF-β3, or fragment or derivative thereof, in accordance with the third aspect of the invention as a medicament.

TGF-β3s of the invention, or biologically active fragments or derivatives thereof, may be used in the treatment of wounds (including chronic wounds such as ulcers). They may particularly be used to promote accelerated wound healing with prevention, reduction or inhibition of scarring, and/or to promote re-epithelialisation of wounds. TGF-β3s of the invention may also be used to effect the prevention or treatment of fibrotic disorders, which may be independently selected from the group comprising pulmonary fibrosis, liver cirrhosis, scleroderma and glomerulonephritis, lung fibrosis, liver fibrosis, skin fibrosis, muscle fibrosis, radiation fibrosis, kidney fibrosis, proliferative vitreoretinopathy and uterine fibrosis.

TGF-β3s of the invention may be used in the treatment of scleroderma, angiogenesis disorders, restenosis, adhesions, endometriosis, ischemic disease, bone and cartilage induction, in vitro fertilisation, oral mucositis and renal disease. By way of example, topical application of wild type, dimeric TGF-β3 has been shown, in animal models and the clinic, to accelerate the healing rate of chronic, non-healing pressure ulcers; reduce the incidence, severity, and duration of oral mucositis; and reduce the adverse side effects of radiation gastrointestinal syndrome resulting from damage to stem cells caused by radiotherapy and chemotherapy during cancer treatment. The inventors believe that TGF-β3s of the invention, or fragments or derivatives thereof, may be used beneficially in all of these indications.

TGF-β3s of the invention may be used in the same way as naturally occurring TGF-β3, for example for the treatment of conditions which may, for example, be selected independently from the group comprising fibrotic disorders, scleroderma, angiogenesis disorders, restenosis, adhesions, endometriosis, ischemic disease, bone and cartilage induction, in vitro fertilisation, oral mucositis, renal disease, prevention, reduction or inhibition of scarring, enhancement of neuronal reconnection in the peripheral and central nervous system, and for preventing, reducing or inhibiting complications of eye surgery (such as LASIK or PRK surgery). TGF-β3s of the invention may be used in the treatment of cleft lip and palate (for example in conjunction with surgical repair of such conditions), and in the reduction or inhibition of scarring and accelerated healing of tendons. The mutant forms of TGF-β3 disclosed in the present invention are able to promote accelerated wound healing and/or prevent, reduce or inhibit scar formation in the same manner as naturally occurring TGF-β3. They are also able to promote epithelial regeneration at sites of epithelial damage.

A "TGF-β3 of the invention" is to be taken to encompass any mutant TGF-β3 in accordance with any of the first, second or third aspects of the present invention. It will be appreciated that TGF-β3s of the invention do not encompass TGF-β1 or TGF-β2. The identity of a TGF-β3 may be determined with reference to its sequence, or preferably with reference to its biological activity. Thus a TGF-β3 may be differentiated from a TGF-β1 or a TGF-β2 on the basis that it is capable of reducing scar formation in a wound to which the TGF-β3 is administered. TGF-β3s in accordance with the present invention may preferably be non-natural TGF-β3s.

A TGF-β3 in accordance with any aspect of the invention may be used in the preparation of a medicament for the treatment of any condition in which it may be wished to utilise TGF-β3. Such uses include, but are not limited to, treatment of any of the conditions considered in the present specification. It may be preferred that TGF-β3s in accordance with the present invention are used in the preparation of medicaments for promoting accelerated healing of wounds, and/or the prevention, reduction or inhibition of scarring. Such scarring may be associated with wounds and/or with fibrotic disorders. Medicaments manufactured using TGF-β3s of the invention may preferably be for use in the skin, or in the eye (for example in the acceleration of healing in the skin or eye, or for the prevention, reduction or inhibition of scarring in the skin or eye).

TGF-β3s in accordance with the invention may be either latent or active TGF-β3s (i.e. either with, or without, the latency associated peptide).

Save for where the context requires otherwise all references to TGF-β3s in accordance with the invention should also be taken to encompass fragments or derivatives of such TGF-β3s, wherein such fragments or derivatives are characterised in that they comprise substitutions (in keeping with the first, second or third aspects of the invention as appropriate) that differentiate them from fragments or derivatives derivable from wild type TGF-β3 (the amino acid sequences of which is taken for the present purposes to be represented by Sequence ID No. 1). Suitable fragments or derivatives of TGF-β3s in accordance with the first, second or third aspects of the invention may comprise at least 10 amino acid residues, preferably at least 40 amino acid residues, more preferably at least 70 amino acid residues, and most preferably at least 100 amino acid residues.

References in the present specification to TGF-β3s and fragments of TGF-β3s also encompass derivatives of such proteins or fragments, except for where the context requires otherwise.

Without limitation, suitable examples of suitable forms of derivatives may be selected from the group consisting of: therapeutically effective peptide derivatives of TGF-β3s of the invention (or their fragments); therapeutically effective fragments or derivatives comprising or based on the pharmacophore of TGF-β3s of the invention (or their fragments); therapeutically effective peptoid derivatives of TGF-β3s of the invention (or their fragments); therapeutically effective D-amino acid derivatives of TGF-β3s of the invention (or their fragments); therapeutically effective peptidomimetics based on TGF-β3s of the invention (or their fragments); therapeutically effective peptide analogues of TGF-β3s of the invention (or their fragments); therapeutically effective pseudopeptides based on TGF-β3s of the invention (or their fragments); therapeutically effective retro-inverso peptides based on TGF-β3s of the invention (or their fragments); therapeutically effective depsipeptide derivatives based on TGF-β3s of the invention (or their fragments); therapeutically effective β-peptide derivatives based on TGF-β3s of the invention (or their fragments); and therapeutically effective retropeptoid derivatives based on TGF-β3s of the invention (or their fragments).

It will be appreciated that, for the purposes of the present invention "a TGF-β3" may be taken to encompass either the monomeric and dimeric forms of the TGF-β3. The inventors have surprisingly found that TGF-β3s in accordance with the present invention are able to exert their biological effects in both monomeric and dimeric form. This contrasts surprisingly with that which has previously been reported in the prior art, where it is generally considered that TGF-βs such as TGF-β3 may only exert biological activity when in dimeric form. The inventors' finding that TGF-β3s in accordance with the present invention may be utilised in monomeric form provides great advantages in that such monomeric forms may be generated through relatively simple folding techniques (examples of which are discussed further below) thereby increasing the speed with which biologically active molecules may be generated, whilst also reducing the costs associated with the generation of such molecules.

It may be preferred that a monomeric TGF-β3 of the invention be a TGF-β3 as set out in Sequence ID Nos. 3, 5, 7, 9 or 11, or a fragment or derivative thereof.

A "medicament of the invention" is to be taken to comprise any medicament that comprises a TGF-β3 in accordance with the invention. A medicament of the invention may additionally or alternatively be a medicament that comprises a nucleic acid encoding a TGF-β3 in accordance with the invention. This encompasses both medicaments per se (i.e. irrespective of the use to which the medicament is to be put), and medicaments for use in specific therapeutic applications (for example, in the treatment or amelioration of the conditions considered in the present specification). It is also intended that medicaments of the invention should be understood to encompass medicaments that comprise suitable fragments or derivatives of TGF-β3s of the invention, or nucleic acids encoding such fragments or derivatives.

A "method of treatment of the invention" (or "method of the invention") is to be taken to comprise any method of treatment that utilises a therapeutically effective amount of a TGF-β3 in accordance with the invention, or a nucleic acid encoding such a TGF-β3. It is also intended that methods of treatment of the invention should be understood to encompass methods of treatment that utilise suitable fragments or derivative of TGF-β3s of the invention, or nucleic acids encoding such fragments or derivative.

Medicaments comprising TGF-β3s of the invention, or biologically active fragments or derivatives thereof, may be used in the treatment of wounds (including chronic wounds such as ulcers). They may particularly be used to promote accelerated wound healing with prevention, reduction or inhibition of scarring, and/or to promote re-epithelialisation of wounds. TGF-β3s of the invention may also be used to effect the prevention or treatment of fibrotic disorders such as pulmonary fibrosis, liver cirrhosis and fibrosis, scleroderma, glomerulonephritis, skin fibrosis, radiation fibrosis, renal fibrosis, proliferative vitreoretinopathy or uterine fibrosis.

TGF-β3s of the invention may be used in the treatment of conditions selected independently from the group consisting of: scleroderma, angiogenesis disorders, restenosis, adhesions, endometriosis, ischemic disease, bone and cartilage induction, in vitro fertilisation, oral mucositis, renal disease, pulmonary fibrosis, liver cirrhosis and fibrosis, glomerulonephritis, skin fibrosis, radiation fibrosis, renal fibrosis and uterine fibrosis. By way of example, topical application of wild type, dimeric TGF-β3 has been shown, in animal models and the clinic, to accelerate the healing rate of chronic, non-healing pressure ulcers; reduce the incidence, severity, and duration of oral mucositis; and reduce the adverse side effects of radiation gastro-intestinal syndrome resulting from damage to stem cells caused by radiotherapy and chemotherapy during cancer treatment. The inventors believe that TGF-β3s of the invention, or fragments or derivatives thereof, may be used beneficially in all of these indications.

The biological activity to be exhibited by a TGF-β3, or fragment or derivative thereof, in accordance with the present invention may preferably be the anti-scarring activity of TGF-β3, and this activity may preferably be investigated in vivo.

A therapeutically effective amount of a TGF-β3, or a fragment or derivative thereof, in accordance with the present invention is an amount sufficient to bring about a required:

i) acceleration in wound healing and/or inhibition of scarring; or
ii) promotion of epithelial regeneration; or
iii) prevention and/or treatment of a fibrotic disorder.

The extent of acceleration of wound healing and/or inhibition of scarring, or epithelial regeneration that may be required will be apparent to, and indeed may readily be determined by, for example, a clinician responsible for the care of the patient. A suitable assessment of the extent of acceleration of wound healing and/or the inhibition of scarring, or promotion of epithelial regeneration, may be determined by the clinician, and may be with reference to suggested methods of measurement described herein.

Suitable TGF-β3s in accordance with the invention, as well as preferred fragments or derivatives of such TGF-β3s, may be selected with reference to any or all of the considerations described herein.

The ability of TGF-β3s of the invention to accelerate the healing of wounds may be readily appreciated and/or measured with reference to properties exhibited by treated wounds. For present purposes a "treated wound" may be considered to be a wound exposed to a therapeutically effective amount of a medicament of the invention, or which has received treatment in accordance with the methods of the invention.

Acceleration of the healing of treated wounds may be illustrated by an increased rate of epithelialisation as compared to control wounds. Thus the methods and medicaments of the invention promote a more rapid re-constitution of a functional epithelial layer over a wounded area than would otherwise be the case.

Alternatively or additionally, accelerated healing of treated wounds may be illustrated by decreased width compared to control wounds at comparable time points. It will be appreciated that this reduction in wound width ensures that there is a relatively faster rate of wound closure (since there is less width of wound to be closed) and is indicative of the ability of such medicaments to accelerate the healing response. Narrower wounds may result in narrower scars that are aesthetically preferable to wider scars Accordingly, accelerated wound healing in the context of the present invention should be taken to encompass any increase in the rate of healing of a treated wound as compared with the rate of healing occurring in control-treated or untreated wounds. Preferably the acceleration of wound healing may be assessed with respect to either comparison of the rate of re-epithelialisation achieved in treated and control wounds, or comparison of the relative width of treated and control wounds at comparable time points. More preferably accelerated wound healing may be defined as comprising both an increased rate of re-epithelialisation and a reduction of wound width compared to control wounds at comparable time points.

Preferably the promotion of accelerated wound healing may give rise to a rate of wound healing that is at least 5%, 10%, 20% or 30% greater than the rate of healing occurring in a control or untreated wound. More preferably the promotion of accelerated wound healing may give rise to a rate of healing that is at least 40%, 50% or 60% greater than healing in a control wound. It is even more preferred that promotion of accelerated wound healing may give rise to a rate of healing that is at least 70%, 80%, or 90% greater than that occurring in control wounds, and most preferably the promotion of accelerated wound healing may give rise to a rate of healing that is at least 100% greater than the rate occurring in control wounds.

There exist a wide range of wound healing disorders that are characterised, or at least partially characterised, by inappropriate failure, delay or retardation of the normal wound healing response. The ability of certain methods and medicaments of the invention to promote accelerated wound healing are thus of utility in the prevention or treatment of such disorders.

Since certain methods and medicaments of the invention are able to bring about the acceleration of wound healing through the promotion of a stimulated re-epithelialisation response (thereby increasing the rate at which the wound closes) it will be appreciated that these methods and medicaments of the invention are particularly advantageous for treatment of wounds of patients that may otherwise be prone to defective, delayed or otherwise impaired re-epithelialisation. For example, it is well known that dermal wounds in the aged exhibit a less-vigorous re-epithelialisation response than do those of younger individuals. There are also many other conditions or disorders in which wound healing is associated with delayed or otherwise impaired re-epithelialisation. For example patients suffering from diabetes, patients with polypharmacy (for example as a result of old age), post-menopausal women, patients susceptible to pressure injuries (for example paraplegics), patients with venous disease, clinically obese patients, patients receiving chemotherapy, patients receiving radiotherapy, patients receiving steroid treatment or immuno-compromised patients may all suffer from wound healing with impaired re-epithelialisation. In many such cases the lack of a proper re-epithelialisation response contributes to the development of infections at the wound site, which may in turn contribute to the formation of chronic wounds such as ulcers. Accordingly it will be appreciated that such patients are particularly likely to benefit from suitable methods or medicaments of the invention.

Chronic wounds are perhaps the most important example of disorders associated with a delayed wound healing response. A wound may be defined as chronic if it does not show any healing tendency within eight weeks of formation when subject to appropriate (conventional) therapeutic treatment. Well-known examples of chronic wounds include venous ulcers, diabetic ulcers and decubitus ulcers, however chronic wounds may arise from otherwise normal acute injuries at any time. Typically chronic wounds may arise as a result of infection of the wound site, inadequate wound treatment, or as a sequitur of progressive tissue breakdown caused by venous, arterial, or metabolic vascular disease, pressure, radiation damage, or tumour.

It will be appreciated that methods and medicaments of the invention capable of accelerating wound healing may be utilised in the treatment of existing chronic wounds in order to promote their healing. Such methods and medicaments may promote the re-epithelialisation of chronic wounds, thereby bringing about healing and closure of the disorder. Preferred methods and medicaments of the invention (such as those utilising TGF-β3s comprising Sequence ID Nos. 3, 5, 7, 9 or 11) may also inhibit scarring associated with wound healing. The prevention of scarring in such contexts may be particularly advantageous since chronic wounds may typically extend over relatively large portions of a patient's body.

In addition, or alternatively, to their use in the treatment of existing chronic wounds, suitable methods and medicaments of the invention may be used to prevent acute wounds of patients predisposed to impaired wound healing developing into chronic wounds. Since suitable methods and medicaments of the invention are able to promote epithelial coverage of the damaged site they are able to reduce the likelihood of a treated wound becoming infected. Similarly, this promotion of re-epithelialisation may be of benefit in the treatment of chronic wounds arising as a result of other conditions such as diabetes or venous disease.

A further group of patients that may derive particular benefit from the methods and medicaments of the invention are those in which the immune system is compromised (for example patients undergoing chemotherapy or radiotherapy, or those suffering from HIV infection). It is well recognised that wounds of immunocompromised patients, who may be unable to mount a normal inflammatory response after wounding, tend to be associated with poor healing outcomes. Such patients may benefit from treatment with suitable methods and medicaments of the invention.

The ability of TGF-β3s of the invention, such as those comprising Sequence ID Nos. 3, 5, 7, 9 or 11, to promote accelerated wound healing while preventing, reducing or inhibiting scarring is also of use in more general clinical contexts. Examples of these further benefits may be considered with reference to the healing of wounds by primary, secondary or tertiary intention, as described below.

For the purposes of the present invention, healing by primary intention may be considered to involve the closure by surgical means (such as sutures, adhesive strips or staples) of opposing edges of a wound. Healing by primary intention is typically employed in the treatment of surgical incisions or other clean wounds, and is associated with minimal levels of tissue loss. The skilled person will recognise that since TGF-β3s in accordance with the invention (such as those comprising Sequence ID Nos. 3, 5, 7, 9 or 11) are capable of reducing wound width they facilitate the joining of opposing wound edges, and thus may be beneficial in wound healing by primary intention. Furthermore, such methods or medicaments may (as described further below) result in the prevention, reduction or inhibition of scarring that may otherwise occur on such healing. The inventors believe that treatment in this manner may have an impact on both the macroscopic and microscopic appearance of scars formed from treated wounds; macroscopically the scars may be less noticeable and blend with the surrounding skin, microscopically the scars may exhibit a regeneration of a more normal skin structure.

For the purposes of the present invention healing by secondary intention may be considered to constitute the closure of wounds by the wound healing process, without direct surgical intervention. Wounds to be healed by secondary intention may be subject to continued care (for example the dressing and re-dressing of the wound as well as the application of suitable medicaments), but it is the natural processes of granulation tissue formation and re-epithelialisation that bring about the closure of the wound. It will be appreciated that since TGF-β3s of the invention (such as those comprising Sequence ID Nos. 3, 5, 7, 9 or 11) are able to increase the rate of re-epithelialisation as compared to that occurring in control wounds they have utility in the promotion of wound healing by secondary intention.

Healing by tertiary intention may be considered to comprise the surgical closure of a wound that has previously been left open to allow at least partial granulation tissue formation and re-epithelialisation. The properties of preferred methods and medicaments of the invention that make them suitable for use in healing by primary or secondary intention are also beneficial in the context of promoting wound healing by tertiary intention.

The use of TGF-β3s of the invention such as Sequence ID Nos. 3, 5, 7, 9 or 11 to stimulate re-epithelialisation (as part of their promotion of accelerated wound healing) while inhibiting scarring is also particularly effective in the treatment of wounds associated with grafting procedures. Treatment using such methods and medicaments of the invention is of benefit both at a graft donor site (where it can aid the re-establishment of a functional epithelial layer while preventing, reducing or inhibiting scar formation), and also at graft recipient sites (where the anti-scarring effects of the treatment inhibit scar formation, while the accelerated healing promotes integration of the grafted tissue). The inventors believe that the methods and medicaments of the invention confer advantages in the contexts of grafts utilising skin, artificial skin, or skin substitutes.

The inventors have found that the methods and medicaments of the invention utilising TGF-β3s comprising Sequence ID Nos. 3, 5, 7, 9 or 11 are able to promote accelerated wound healing with inhibition of scarring when administered either prior to wounding, or once a wound has already been formed.

The inventors have found that methods or medicaments of the invention utilising TGF-β3s, such as those comprising Sequence ID Nos. 3, 5, 7, 9 or 11, are capable of promoting epithelial regeneration. The promotion of epithelial regeneration within the context of the present invention may be understood to encompass any increase in the rate of epithelial regeneration as compared to the regeneration occurring in a control-treated or untreated epithelium.

The rate of epithelial regeneration attained using suitable methods or medicaments in accordance with the invention may readily be compared with that taking place in control-treated or untreated epithelia using any suitable model of epithelial regeneration known in the art. For example, the rate at which sites of experimental epithelial damage having known areas regenerate may be compared using well known in vivo models in mice, rats, rabbits or pigs such as those described in Tomlinson and Ferguson (2003), Davidson et al. (1991) and Paddock et al. (2003).

Without wishing to be bound by any hypothesis the inventors believe that the promotion of epithelial regeneration achieved by TGF-β3s of the invention is mediated by their promotion of epithelial cell migration. The epithelial cells (the migration of which has been promoted) are thereby able to re-populate and regenerate the damaged epithelium more rapidly than occurs in the absence of treatment.

It will be appreciated that promotion of epithelial regeneration using TGF-β3s of the invention may be of use to induce effective re-epithelialisation in contexts in which the re-epithelialisation response is impaired, inhibited, retarded or otherwise defective. Promotion of epithelial regeneration may be also effected to accelerate the rate of defective or normal epithelial regeneration responses in patients suffering from epithelial damage.

There are many contexts in which the body's re-epithelialisation response may be defective. For example, defective re-epithelialisation in the skin is associated with conditions such as pemphigus, Hailey-Hailey disease (familial benign pemphigus), toxic epidermal necrolysis (TEN)/Lyell's syndrome, epidermolysis bullosa, cutaneous leishmaniasis and actinic keratosis. Defective re-epithelialisation of the lungs may be associated with idiopathic pulmonary fibrosis (IPF) or interstitial lung disease. Defective re-epithelialisation of the eye may be associated with conditions such as partial limbal stem cell deficiency or corneal erosions. Defective re-epithelialisation of the gastrointestinal tract or colon may be associated with conditions such as chronic anal fissures (fissure in ano), ulcerative colitis or Crohn's disease, and other inflammatory bowel disorders.

As has been set out above, TGF-β3s of the present invention may be used to prevent, reduce or otherwise inhibit scarring. This inhibition of scarring can be effected at any body site and any tissue or organ, including the skin, eye, nerves, tendons, ligaments, muscle, and oral cavity (including the lips and palate), as well as internal organs (such as the liver, heart, brain, abdominal cavity, pelvic cavity, thoracic cavity, guts and reproductive tissue). In the skin, treatment may improve the macroscopic and microscopic appearance of scars; macroscopically the scars may be less visible and blend with the surrounding skin, microscopically the collagen fibres within the scar may have morphology and organisation that is more similar to those in the surrounding skin. The prevention, reduction or inhibition of scarring within the context of the present invention should be understood to encompass any degree of prevention, reduction or inhibition in scarring as compared to the level of scarring occurring in a control-treated or untreated wound (as defined elsewhere in the specification). Except where the context requires otherwise references to "prevention", "reduction" or "inhibition" of scarring may be taken to equivalent mechanisms that are all manifested in anti-scarring activity.

The prevention, reduction or inhibition of dermal scarring achieved using methods and medicaments of the invention may be assessed and/or measured with reference to either the microscopic or, preferably, macroscopic appearance of a treated scar as compared to the appearance of an untreated scar. More preferably the prevention, reduction or inhibition of scarring may be assessed with reference to both macroscopic and microscopic appearance of a treated scar. For the present purposes a "treated scar" may be defined as a scar formed on healing of a treated wound, whereas an "untreated scar" may be defined as the scar formed on healing of an untreated wound, or a wound treated with placebo or standard care. Suitable comparison scars may preferably be matched to the treated scar with reference to scar age, site, size and patient.

In considering the macroscopic appearance of a scar resulting from a treated wound, the extent of scarring, and hence the magnitude of any prevention, inhibition or reduction in scarring achieved, may be assessed with reference to any of a number of parameters.

Suitable parameters for the macroscopic assessment of scars may include:

i) Colour of the scar. As noted above, scars may typically be hypopigmented or hyperpigmented with regard to the surrounding skin. Inhibition or reduction of scarring may be demonstrated when the pigmentation of a treated scar more closely approximates that of unscarred skin than does the pigmentation of an untreated scar. Similarly, scars may be redder than the surrounding skin. In this case inhibition or reduction of scarring may be demonstrated when the redness of a treated scar fades earlier, or more completely, or to resemble more closely the appearance of the surrounding skin, compared to an untreated scar.

ii) Height of the scar. Scars may typically be either raised or depressed as compared to the surrounding skin. Inhibition or reduction of scarring may be demonstrated when the height of a treated scar more closely approximates that of unscarred skin (i.e. is neither raised nor depressed) than does the height of an untreated scar.

iii) Surface texture of the scar. Scars may have surfaces that are relatively smoother than the surrounding skin (giving rise to a scar with a "shiny" appearance) or that are rougher than the surrounding skin. Inhibition or reduction of scarring may be demonstrated when the surface texture of a treated scar more closely approximates that of unscarred skin than does the surface texture of an untreated scar.

iv) Stiffness of the scar. The abnormal composition and structure of scars means that they are normally stiffer than the undamaged skin surrounding the scar. In this case, inhibition or reduction of scarring may be demonstrated when the stiffness of a treated scar more closely approximates that of unscarred skin than does the stiffness of an untreated scar.

A treated scar will preferably demonstrate prevention, inhibition or reduction of scarring as assessed with reference to at least one of the parameters for macroscopic assessment set out above. More preferably a treated scar may demonstrate prevented, inhibited or reduced scarring with reference to at least two of the parameters, even more preferably at least three of the parameters, and most preferably all four of these parameters. An overall assessment of scarring may be made using, for example, a Visual Analogue Scale or a digital assessment scale.

Suitable parameters for the microscopic assessment of scars may include:

i) Thickness of extracellular matrix (ECM) fibres. Scars typically contain thinner ECM fibres than are found in the surrounding skin. This property is even more pronounced in the case of keloid and hypertrophic scars. Inhibition or reduction of scarring may be demonstrated when the thickness of ECM fibres in a treated scar more closely approximates the thickness of ECM fibres found in unscarred skin than does the thickness of fibres found in an untreated scar.

ii) Orientation of ECM fibres. ECM fibres found in scars tend to exhibit a greater degree of alignment with one another than do those found in unscarred skin (which have a random orientation frequently referred to as "basket weave"). The ECM of pathological scars such as keloids and hypertrophic scars may exhibit even more anomalous orientations, frequently forming large "swirls" or "capsules" of ECM molecules. Accordingly, inhibition or reduction of scarring may be demonstrated when the orientation of ECM fibres in a treated scar more closely approximates the orientation of ECM fibres found in unscarred skin than does the orientation of such fibres found in an untreated scar.

iii) ECM composition of the scar. The composition of ECM molecules present in scars shows differences from that found in normal skin, with a reduction in the amount of elastin present in ECM of scars. Thus inhibition or reduction of scarring may be demonstrated when the composition of ECM fibres in the dermis of a treated scar more closely approximates the composition of such fibres found in unscarred skin than does the composition found in an untreated scar.

iv) Cellularity of the scar. Scars tend to contain relatively fewer cells than does unscarred skin. It will therefore be appreciated that inhibition or reduction of scarring may be demonstrated when the cellularity of a treated scar more closely approximates the cellularity of unscarred skin than does the cellularity of an untreated scar.

A treated scar will preferably demonstrate prevention, reduction or inhibition of scarring as assessed with reference to at least one of the parameters for microscopic assessment set out above. More preferably a treated scar may demonstrate prevention, reduction or inhibition of scarring with reference to at least two of the parameters, even more preferably at least three of the parameters, and most preferably all four of these parameters.

Prevention, reduction or inhibition of scarring of a treated wound may further be assessed with reference to suitable parameters used in the:

i) macroscopic clinical assessment of scars, particularly the assessment of scars upon a subject;
ii) assessment of photographic images of scars;
iii) assessment of silicone moulds or positive plaster casts made from silicone moulds of scars; and
iv) microscopic assessment of scars, for example by histological analysis of the microscopic structure of scars.

It will be appreciated that prevention, reduction or inhibition of scarring of a treated wound may be indicated by improvement of one or more of such suitable parameters, and that in the case of prevention, reduction or inhibition, as assessed with reference to a number of parameters, that these parameters may be combined from different assessment schemes (e.g. reduction inhibition or improvement in at least one parameter used in macroscopic assessment and at least one parameter used in microscopic assessment).

Prevention, reduction or inhibition of scarring may be demonstrated by an improvement in one or more parameters indicating that a treated scar more closely approximates unscarred skin with reference to the selected parameter(s) than does an untreated or control scar.

Suitable parameters for the clinical measurement and assessment of scars may be selected based upon a variety of measures or assessments including those described by Beausang et al (1998) and van Zuijlen et al (2002).

Typically, suitable parameters may include:

1. Assessment with Regard to Visual Analogue Scale (VAS) Scar Score.

Prevention, reduction or inhibition of scarring may be demonstrated by a reduction in the VAS score of a treated scar when compared to a control scar. A suitable VAS for use in the assessment of scars may be based upon the method described by Beausang et al (1998).

2. Scar Height, Scar Width, Scar Perimeter, Scar Area or Scar Volume.

The height and width of scars can be measured directly upon the subject, for example by use of manual measuring devices such as callipers. Scar width, perimeter and area may be measured either directly on the subject or by image analysis of photographs of the scar. The skilled person will also be aware of further non-invasive methods and devices that can be used to investigate suitable parameters, including silicone moulding, ultrasound, optical three-dimensional profilimetry and high resolution Magnetic Resonance Imaging.

Prevention, reduction or inhibition of scarring may be demonstrated by a reduction in the height, width, area or volume, or any combination thereof, of a treated scar as compared to an untreated scar.

3. Appearance and/or Colour of Scar Compared to Surrounding Unscarred Skin.

The appearance or colour of a treated scar may be compared to that of surrounding unscarred skin, and the differences (if any) compared with the difference between the appearance and colour of untreated scars and unscarred skin. Such a comparison may be made on the basis of a visual assessment of the respective scars and unscarred skin. The appearance of a scar may be compared with unscarred skin with reference to whether the scar is lighter or darker than the unscarred skin. The respective colours of the scars and skin may be perfectly matched to one another, slightly mismatched, obviously mismatched or grossly mismatched.

Alternatively or additionally to visual assessment, there are a number of non-invasive colourimetry devices which are able to provide data with respect to pigmentation of scars and unscarred skin, as well as redness of the skin (which may be an indicator of the degree of vascularity present in the scar or skin). Examples of such devices include the Minolta Chronameter CR-200/300; Labscan 600; Dr. Lange Micro Colour; Derma Spectrometer; laser-Doppler flow meter; and Spectrophotometric Intracutaneous Analysis (SIA) scope.

Prevention, reduction or inhibition of scarring may be demonstrated by a smaller magnitude of difference between the appearance or colour of treated scars and unscarred skin than between untreated scars and unscarred skin.

4. Scar Distortion and Mechanical Performance

Scar distortion may be assessed by visual comparison of a scar and unscarred skin. A suitable comparison may classify a selected scar as causing no distortion, mild distortion, moderate distortion or severe distortion.

The mechanical performance of scars can be assessed using a number of non-invasive methods and devices based upon suction, pressure, torsion, tension and acoustics. Suitable examples include of known devices capable of use in assessing mechanical performance of scars include Indentometer, Cutometer, Reviscometer, Visco-elastic skin analysis, Dermaflex, Durometer, Dermal Torque Meter, Elastometer.

Prevention, reduction or inhibition of scarring may be demonstrated by a reduction in distortion caused by treated scars as compared to that caused by untreated scars. It will also be appreciated that prevention, reduction or inhibition of scarring may be demonstrated by the mechanical performance of unscarred skin being more similar to that of treated scars than of untreated scars.

5. Scar Contour and Scar Texture

Scar contour may be investigated by means of visual assessment. Suitable parameters to consider in such an assessment include whether or not a scar is flush with surrounding skin, slightly proud, slightly indented, hypertrophic or keloid. The texture of a scar may be assessed with reference to the scar's appearance, and this may also be undertaken by a visual assessment as to whether the scar is, for instance, matt or shiny or has a roughened or smooth appearance as compared to unscarred skin.

Scar texture may additionally be assessed with reference to whether the scar has the same texture as unscarred skin (normal texture), is just palpable, firm or hard compared to unscarred skin. The texture of scars may also be assessed with reference to the Hamilton scale (described in Crowe et al, 1998).

In addition to the techniques set out above, there are a number of non-invasive profilimetry devices that use optical or mechanical methods for assessment of scar contour and/or texture. Such assessments may be carried out on the body of the subject or, for example, on silicone mould impressions of scars, or on positive casts made from such impressions.

Prevention, reduction or inhibition of scarring may be demonstrated in the event that treated scars have scar profiles and textures more comparable to unscarred skin than do untreated scars.

Photographic Assessments

Independent Lay Panel

Photographic assessment of treated and untreated scars may be performed by an independent lay panel of assessors using standardised and calibrated photographs of the scars. The scars may be assessed by an independent lay panel to provide categorical ranking data (e.g. that a given treated scar is "better", "worse" or "no different" when compared to an untreated scar) and quantitative data using a Visual Analogue Scale (VAS) based upon the method described by Beausang et al (1998). The capture of these data may make use of suitable software and/or electronic system(s) as described in the applicant's co-pending patent application.

Expert Panel

Photographic assessment of treated and untreated scars may alternatively or additionally be performed by a panel of expert assessors using standardised and calibrated photographs of the scars to be assessed. The panel of experts may preferably consist of suitable individuals skilled in the art such as plastic surgeons and scientists of suitable backgrounds.

Such assessment may provide categorical data, as described above or with respect to the comparison of a timecourse of images of selected treated and untreated scars.

Suitable assessments to be made may include:

Identification of the best scar, which for the purposes of the present invention may be considered that scar which most closely resembles the surrounding skin. Once the best scar has been identified the magnitude of the difference between scars may be considered, for example is the difference between scars slight or obvious. Further parameters that may be considered include the earliest time after scar formation at which a difference between scars may be detected, the time post-formation at which the difference between scars is most obvious (or alternatively the finding that the difference continues after the last timepoint assessed), as well as considering whether or not the better scar remains consistently better.

Consideration may also be given to whether or not one scar is consistently redder than the other, and whether the redness fades over the timepoints considered (or continues after the last timepoint) and if so at what time after scar formation. An expert panel may also consider at what time after formation any difference in redness becomes detectable, as well as the time post-formation at which the difference in redness is most obvious.

An expert panel may also consider whether or not one of a treated or untreated scar is consistently whiter than the other, or whiter than unscarred skin. In the event that a difference in whiteness is detectable consideration may be given to the time after scar formation at which the difference may be detected, the time at which the difference is most obvious, and the time at which the difference disappears.

A further parameter that may be assessed by an expert panel is the texture of treated and untreated scars. In comparing treated and untreated scars the expert panel may consider which of the scars has the best skin texture, the earliest time after scar formation at which any difference present may be detected, the time post-formation at which any difference is most obvious, and the time at which any difference disappears Comparison of treated and untreated scars may further assess which of the scars is narrowest, and which of the scars is shortest. Consideration may also be given to the shape of the scar and the proportion of the scar margin that is distinguishable from the surrounding skin. As with previously described visual assessments and assessments of colour the presence, degree and location of hyper-pigmentation may also be considered.

As noted above, one of the ways in which the quality of treated and untreated scars may be compared is by microscopic assessment. Microscopic assessment of scar quality may typically be carried out using histological sections of scars. The process of microscopically assessing and measuring scars may take into consideration categorical data based on the following suitable parameters:

1. Epidermal restitution. Particular attention may be paid to the degree of restoration of the rete ridges, and to the thickness of the restored epidermis.
2. Angiogenesis and Inflammation. Consideration may be given to the number of blood vessels present, the size of the blood vessels present and evidence of inflammation, including an assessment of any level of inflammation present.
3. Collagen organisation. In assessing collagen organisation reference may be made to the orientation of collagen fibres present in the scar, the density of such fibres and collagen fibre thickness in the papillary and reticular dermis.
4. Visual analogue scale (VAS) assessment of collagen organisation for the papillary dermis and for the reticular dermis may also provide a useful index of scar quality.
5. Other features that may be taken into account in assessing the microscopic quality of scars include elevation or depression of the scar relative to the surrounding unscarred skin, and the prominence or visibility of the scar at the normal dermal interface.
6. It will be seen that the assessments described above allow the generation of scar ranking data which is able to provide an indication as to whether a treated scar is better, worse or no different compared to a control, untreated or other suitable comparator scar.

In addition to categorical data, quantitative data (preferably relating to the above parameters) can be generated using image analysis in combination with suitable visualisation techniques. Examples of suitable visualisation techniques that may be employed in assessing scar quality are specific histological stains or immuno-labelling, wherein the degree of staining or labelling present may be quantitatively determined by image analysis Quantitative data may be usefully and readily produced in relation to the following parameters:

1. Scar width, height, elevation, volume and area.
2. Epithelial thickness and coverage (for example the area of epidermis present in a scar or the proportion of a wound with epidermal coverage).
3. Number, size, area (i.e. cross-section) and location of blood vessels.
4. Degree of inflammation, number, location and populations/types of inflammatory cells present.
5. Collagen organisation, collagen fibre thickness, collagen fibre density.

Prevention, reduction or inhibition of scarring may be demonstrated by a change in any of the parameters considered above such that a treated scar more closely resembles unscarred skin than does a control or untreated scar (or other suitable comparator).

The assessments and parameters discussed are suitable for comparisons of the effects of peptide as compared to control, placebo or standard care treatment in animals or humans. Appropriate statistical tests may be used to analyse datasets generated from different treatments in order to investigate significance of results.

Preferably prevention, reduction or inhibition of scarring may be demonstrated with reference to more than one parameter. More preferably prevention, reduction or inhibition of scarring may be demonstrated with reference to both a clinical (i.e. observed on the subject) parameter and a photographic parameter. Even more preferably prevention, reduction or inhibition of scarring may be demonstrated with reference to a clinical parameter, a photographic parameter, and also a microscopic assessment parameter (for instance a histological parameter). Most preferably prevention, reduction or inhibition of scarring may be demonstrated with reference to a clinical VAS score, external lay panel VAS score and ranking (from photographic images) and microscopic VAS score of the reticular dermis.

The use of suitable methods and medicaments of the invention is able to bring about a rapid improvement in the cosmetic appearance of an injured area thus treated. Cosmetic considerations are important in a number of clinical contexts, particularly when wounds are formed at prominent body sites such as the face, neck and hands. Consequently the inhibition of scarring (which may preferably be in combination with accelerated wound healing) at such sites where it is desired to improve the cosmetic appearance of the scar formed represents a preferred embodiment of the invention.

In addition to its cosmetic impact skin scarring is responsible for a number of deleterious effects afflicting those suffering from such scarring. For example, skin scarring may be associated with reduction of physical and mechanical function, particularly in the case of contractile scars (such as hypertrophic scars) and/or situations in which scars are formed across joints. In these cases the altered mechanical properties of scarred skin, as opposed to unscarred skin, and the effects of scar contraction may lead to dramatically restricted movement of a joint (articulation) so effected. Accordingly it is a preferred embodiment that suitable medicaments and methods of the invention be used to prevent, reduce or inhibit scarring of wounds covering joints of the body (preferably also accelerating healing of such wounds). In another preferred embodiment suitable medicaments and methods of the invention may be used to promote accelerated wound healing and/or prevent, reduce or inhibit scarring of wounds at increased risk of forming a contractile scar.

The extent of scar formation, and hence extent of cosmetic or other impairment that may be caused by the scar, may also be influenced by factors such as the tension of the site at which the wound is formed. For example, it is known that skin under relatively high tension (such as that extending over the chest, or associated with lines of tension) may be prone to formation of more severe scars than at other body sites. Thus in a preferred embodiment suitable medicaments and methods of the invention may be used to promote accelerated wound healing and/or prevent, reduce or inhibit scarring of wounds located at sites of high skin tension. There are many surgical procedures that may be used in scar revision to allow realignment of wounds and scars such that they are subject to reduced tension. Probably the best known of these is "Z-plasty" in which two V-shaped flaps of skin are transposed to allow rotation of a line of tension. Thus in a more preferred embodiment such medicaments and methods of the invention be used to promote accelerated wound healing and/or prevent, reduce or inhibit scarring of wounds during surgical revision of disfiguring scars.

Pathological scarring may have more pronounced deleterious effects than arise even as a result of relatively severe normal scarring. Common examples of pathological scars include hypertrophic scars and keloids. It is recognised that certain types of wound, or certain individuals may be predisposed to pathological scar formation. For instance individuals of Afro-Caribbean, Japanese or Mongloid heritage, or those having a familial history of pathological scarring may be considered to be at increased risk of hypertrophic scar or keloid formation. Wounds of children, and particularly burns wounds of children, are also associated with increased hypertrophic scar formation. Accordingly it is a preferred embodiment of the invention that suitable medicaments and methods be used to promote accelerated wound healing and/or prevent, reduce or inhibit scarring of wounds in which there is an increased risk of pathological scar formation.

Although individuals already subject to pathological scarring suffer from a predisposition to further excessive scar formation it is often clinically necessary to surgically revise hypertrophic scars or keloids, with an attendant risk of consequential pathological scar formation. Thus it is a further preferred embodiment of the invention that suitable medicaments and methods be used to promote accelerated wound healing and/or prevent, reduce or inhibit scarring of wounds produced by surgical revision of pathological scars.

It is recognised that wounds resulting from burns injuries (which for the purposes of the present invention may be taken also to encompass scalding injuries involving hot liquids or gasses) may extend over great areas of an individual so afflicted. Accordingly, burns may give rise to scar formation covering a large proportion of a patient's body, thereby increasing the risk that the scar formed will cover areas of elevated cosmetic importance (such as the face, neck, arms or hands) or of mechanical importance (particularly the regions covering or surrounding joints). Burns injuries caused by hot liquids are frequently suffered by children (for example as a result of upsetting pans, kettles or the like) and, due to the relatively smaller body size of children, are particularly likely to cause extensive damage over a high proportion of the body area. It is a further preferred embodiment of the invention that suitable medicaments and methods be used to promote accelerated wound healing and/or prevent, reduce or inhibit scarring of wounds produced by burns injuries.

As noted above, wound healing in response to burns injuries is frequently associated with adverse scarring outcomes, such as the formation of hypertrophic scars. A further consequence of the relatively large size of burns injuries is that they are particularly susceptible to complications such as infection and desiccation that arise due to lack of a functional epithelial layer. In the light of the above it will be appreciated that suitable methods and medicaments of the invention may be used in the treatment of burn injuries to reduce the level of scarring that occurs as a result of the wound and/or accelerate the re-constitution of a functional epithelial barrier.

The inventors have found that methods and medicaments of the invention utilising TGF-β3s of the invention are able to promote re-epithelialisation. Accordingly such methods and medicaments are particularly effective in the treatment of all injuries involving damage to an epithelial layer. Such injuries are exemplified by, but not limited to, injuries to the skin, in which the epidermis is damaged. It will however be appreciated that such methods and medicaments of the invention are also applicable to other types of wounds in which epithelia are damaged, such as injuries involving the respiratory epithelia, digestive epithelia or epithelia surrounding internal tissues or organs (such as the epithelia of the peritoneum).

The healing of wounds involving the peritoneum (the epithelial covering of the internal organs, and/or the interior of the body cavity) may frequently give rise to adhesions. Such adhesions are a common sequitur of surgery involving gynaecological or intestinal tissues. The inventors believe that the ability of the methods and medicaments of the invention (such as those comprising TGF-β3s set out in Sequence ID Nos. 3, 5, 7, 9 or 11) to accelerate the regeneration of the peritoneum while reducing scarring may reduce the incidence of inappropriate attachment of portions of the peritoneum to one another, and thereby reduce the occurrence of adhesions. Accordingly, the use of such methods and medicaments of the invention to prevent the formation of intestinal or gynaecological adhesions represents a preferred embodiment of the invention. Indeed the use of such methods or medicaments of the invention in the healing of any wounds involving the peritoneum is a preferred embodiment.

The methods or medicaments of the invention may be used prophylactically, for example at sites where no wound exists but where a wound that would otherwise give rise to a scar or chronic wound is to be formed. By way of example medicaments in accordance with the invention may be administered to sites that are to undergo wounding as a result of elective procedures (such as surgery), or to sites that are believed to be at elevated risk of wounding. It may be preferred that the medicaments of the invention are administered to the site around the time of wounding, or immediately prior to the forming of a wound (for example in the period up to six hours before wounding) or the medicaments may be administered at an earlier time before wounding (for example up to 48 hours before a wound is formed). The skilled person will appreciate that the most preferred times of administration prior to formation of a wound will be determined with reference to a number of factors, including the formulation and route of administration of the selected medicament, the dosage of the medicament to be administered, the size and nature of the wound to be formed, and the biological status of the patient (which may determined with reference to factors such as the patient's age, health, and predisposition to healing complications or adverse scarring). The prophylactic use of methods and medicaments in accordance with the invention is a preferred embodiment of the invention, and is particularly preferred in the promotion of accelerated wound healing and/or prevention, reduction or inhibition of scarring in the context of surgical wounds.

The methods and medicaments of the invention are also able to promote accelerated wound healing and/or inhibited scarring if administered after a wound has been formed. It is preferred that such administration should occur as early as possible after formation of the wound, but agents of the invention are able to promote accelerated wound healing and/or prevent, reduce or inhibit scarring at any time up until the healing process has been completed (i.e. even in the event that a wound has already partially healed the methods and medicaments of the invention may be used to promote accelerated wound healing and/or prevent, reduce or inhibit scarring in respect of the remaining un-healed portion). It will be appreciated that the "window" in which the methods and medicaments of the invention may be used to promote accelerated wound healing and/or prevent, reduce or inhibit scarring is dependent on the nature of the wound in question (including the degree of damage that has occurred, and the size of the wounded area). Thus in the case of a large wound the methods and medicaments of the invention may be administered relatively late in the healing response yet still be able to promote accelerated wound healing and/or prevent, reduce or inhibit scarring. The methods and medicaments of the invention may, for instance, preferably be administered within the first 24 hours after a wound is formed, but may still promote accelerated wound healing and/or prevent, reduce or inhibit scarring if administered up to ten, or more, days after wounding.

The methods and medicaments of the invention may be administered on one or more occasions as necessary in order to promote accelerated wound healing and/or prevent, reduce or inhibit scarring. For instance therapeutically effective amounts of the medicaments may be administered to a wound as often as required until the healing process has been completed. By way of example, the medicaments of the invention may be administered daily or twice daily to a wound for at least the first three days following the formation of the wound.

Most preferably the methods or medicaments of the invention may be administered both before and after formation of a wound. The inventors have found that administration of the medicaments of the invention immediately prior to the formation of a wound, followed by daily administration of such agents in the days following wounding, is particularly effective in promoting accelerated wound healing and/or prevent, reduce or inhibit scarring.

For the purposes of the present specification by "agent" or "agent of the invention" are meant biologically or therapeutically active TGF-β3s of the invention; and/or biologically or therapeutically active fragments of TGF-β3s of the invention; and/or biologically or therapeutically active derivatives of TGF-β3s of the invention. Agents of the invention may also include nucleic acids encoding TGF-β3s of the invention (or fragments or derivatives thereof). It will be appreciated that all such agents may be incorporated in medicaments in accordance with the invention, and may be used in the methods or uses of the invention.

It will be appreciated that the amount of a medicament of the invention that should be applied to a wound depends on a number of factors such as the biological activity and bioavailability of the agent present in the medicament, which in turn depends, among other factors, on the nature of the agent and the mode of administration of the medicament. Other factors in determining a suitable therapeutic amount of a medicament may include:

A) The half-life of the agent in the subject being treated.
B) The specific condition to be treated (e.g. acute wounding or chronic wounds).
C) The age of the subject.

The frequency of administration will also be influenced by the above-mentioned factors and particularly the half-life of the chosen agent within the subject being treated.

Generally when medicaments in accordance with the invention are used to treat existing wounds the medicament should be administered as soon as the wound has occurred (or in the case of wounds that are not immediately apparent, such as those at internal body sites, as soon as the wound has been diagnosed). Therapy with methods or medicaments in accordance with the invention should continue until the healing process has been accelerated, and/or scarring prevented, reduced or inhibited, to a clinician's satisfaction.

Frequency of administration will depend upon the biological half-life of the agent used. Typically a cream or ointment containing an agent of the invention should be administered to a target tissue such that the concentration of the agent at a wound is maintained at a level suitable for having a therapeutic effect. This may require administration daily or even several times daily.

Medicaments of the invention, may be administered by any suitable route capable of achieving the desired effect of promoting wound healing and/or preventing, reducing or inhibiting scarring, but it is preferred that the medicaments be administered locally at a wound site.

The inventors have found that the promotion of accelerated wound healing and/or prevention, reduction or inhibition of scarring may be effected by the administration of an agent of the invention by injection at the wound site. For instance, in the case of dermal wounds, agents of the invention may be administered by means of intradermal injection. Thus a preferred medicament in accordance with the invention comprises an injectable solution of an agent of the invention (e.g. for injection around the margins of a site of epithelial damage or a site likely to be damaged). Suitable formulations for use in this embodiment of the invention are considered below.

Alternatively, or additionally, medicaments of the invention may also be administered in a topical form to promote accelerated wound healing and/or prevention, reduction or inhibition of scarring. Such administration may be effected as part of the initial and/or follow up care for the wounded area.

The inventors find that the promotion of accelerated wound healing and/or prevention, reduction or inhibition of scarring is particularly improved by topical application of an agent of the invention to a wound (or, in the case of prophylactic application, to a tissue or site where a wound is to be formed).

Compositions or medicaments containing agents of the invention may take a number of different forms depending, in particular on the manner in which they are to be used. Thus, for example, they may be in the form of a liquid, ointment, cream, gel, hydrogel, powder or aerosol. All of such compositions are suitable for topical application to a wound, which is a preferred means of administering agents of the invention to a subject (person or animal) in need of treatment.

The agents of the invention may be provided on a sterile dressing or patch, which may be used to cover a wound or other site of epithelial damage to be treated.

It will be appreciated that the vehicle of a composition comprising agents of the invention should be one that is well tolerated by the patient and allows release of the agent to the wound. Such a vehicle is preferably biodegradeable, bioresolveable, bioresorbable and/or non-inflammatory.

Medicaments and compositions comprising agents of the invention may be used in a number of ways. Thus, for example, a composition may be applied in and/or around a wound in order to promote accelerated wound healing and/or prevent, reduce or inhibit scarring. If the composition is to be applied to an "existing" wound, then the pharmaceutically acceptable vehicle will be one which is relatively "mild" i.e. a vehicle which is biocompatible, biodegradable, bioresolvable and non-inflammatory.

An agent of the invention, or a nucleic acid encoding such an agent (as considered further below), may be incorporated within a slow or delayed release device. Such devices may, for example, be placed on or inserted under the skin and the agent or nucleic acid may be released over days, weeks or even months. Such a device may be particularly useful for patients (such as those suffering from chronic wounds) that require long-term promotion of accelerated wound healing and/or prevention, reduction or inhibition of scarring. The devices may be particularly advantageous when used for the administration of an agent or nucleic acid that would normally require frequent administration (e.g. at least daily administration by other routes).

Daily doses of an agent of the invention may be given as a single administration (e.g. a daily application of a topical formulation or a daily injection). Alternatively, the agent of the invention may require administration twice or more times during a day. In a further alternative, a slow release device may be used to provide optimal doses of an agent of the invention to a patient without the need to administer repeated doses.

In one embodiment a pharmaceutical vehicle for administration of an agent of the invention may be a liquid and a suitable pharmaceutical composition would be in the form of a solution. In another embodiment, the pharmaceutically acceptable vehicle is a solid and a suitable composition is in the form of a powder or tablet. In a further embodiment the agent of the invention may be formulated as a part of a pharmaceutically acceptable transdermal patch.

A solid vehicle can include one or more substances that may also act as flavouring agents, lubricants, solubilizers, suspending agents, fillers, glidants, compression aids, binders or tablet-disintegrating agents; it can also be an encapsulating material. In powders, the vehicle is a finely divided solid that is in admixture with the finely divided agent of the invention. In tablets, the agent of the invention is mixed with a vehicle having the necessary compression properties in suitable proportions and compacted in the shape and size desired. The powders and tablets preferably contain up to 99% of the agent of the invention. Suitable solid vehicles include, for example, calcium phosphate, magnesium stearate, talc, sugars, lactose, dextrin, starch, gelatin, cellulose, polyvinylpyrrolidine, low melting waxes and ion exchange resins.

Liquid vehicles may be used in preparing solutions, suspensions, emulsions, syrups, elixirs and pressurized compositions. The agent of the invention can be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilizers, emulsifiers, buffers, preservatives, sweeteners, flavouring agents, suspending agents, thickening agents, colours, viscosity regulators, stabilizers or osmo-regulators. Suitable examples of liquid vehicles for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be halogenated hydrocarbon or other pharmaceutically acceptable propellant.

Liquid pharmaceutical compositions which are sterile solutions or suspensions can be utilized by for example, intramuscular, intrathecal, epidural, intraperitoneal, intradermal, intrastromal (cornea) or subcutaneous injection. Sterile solutions can also be administered intravenously. The agent of the invention may be prepared as a sterile solid composition that may be dissolved or suspended at the time of administration using sterile water, saline, or other appropriate sterile injectable medium. Vehicles are intended to include necessary and inert binders, suspending agents, lubricants and preservatives.

In the situation in which it is desired to administer an agent of the invention by means of oral ingestion, it will be appreciated that the chosen agent will preferably be an agent having an elevated degree of resistance to degradation. For example, the agent of the invention may be protected (for instance using the techniques described above) so that its rate of degradation in the digestive tract is reduced.

Compositions of agents of the invention are suitable to be used for promoting accelerated wound healing and/or inhibiting scarring in the cornea. Corneal wounds may result from trauma to the eye arising as a result of accidental injury (as considered above) or as a result of surgical operations (e.g. laser surgery on the cornea). In this case a preferred medicament of the invention may be in the form of an eye drop.

Agents of the invention may be used in a range of "internal" wounds (i.e. wounds occurring within the body, rather than on an external surface). Thus for example, medicaments in accordance with the invention may be formulated for inhalation for use in wounds arising in the lungs or other respiratory epithelia.

Known procedures, such as those conventionally employed by the pharmaceutical industry (e.g. in vivo experimentation, clinical trials etc), may be used to establish specific formulations of compositions comprising agents of the invention and precise therapeutic regimes for administration of such compositions (such as daily doses of the active agent and the frequency of administration).

A suitable daily dose of an agent in accordance with the invention able to promote accelerated wound healing and/or prevention, reduction or inhibition of scarring depends upon a range of factors including (but not limited to) the nature of the tissue wounded, area and/or depth of the wound to be treated, the severity of the wound, and the presence or absence of factors predisposing to pathological scar or chronic wound formation.

By way of example, the total amount of an active agent that may be administered by local injection to a wound or site of epithelial damage may preferably be in the region of 50 ng/100 µL per linear centimeter of wound or epithelial damage. Such a dose may be given once a day for up to three days, thereby providing a total dose of 150 ng/linear centimeter of wound or epithelial damage.

In the case of topical application to acute wounds or sites of epithelial damage, a suitable amount of an active agent may preferably be in the region of 100 ng/cm$^2$. Such a dose may be given once a day for up to 3 days, thereby providing a total dose of 300 ng/cm$^2$ of wound or epithelial damage.

By way of further example, the preferred amount of an active agent to be administered daily to a wound or site of epithelial damage may be in the region of 50 ng/linear centimeter of wound or epithelial damage (if administered by injection), or 100 ng/cm$^2$ of wound or epithelial damage (if administered topically).

By way of still further example, the amount of an active agent that may be administered to a wound or site of epithelial damage in a single incidence of treatment may preferably be in the region of 50-200 ng/linear centimeter of wound or epithelial damage (if administered by injection), or 100-300 ng/cm$^2$ of wound or epithelial damage (if administered topically).

The amount of an agent in accordance with the invention required for the treatment of wounds or other sites of epithelial damage will typically be within the range of 1 pg to 1 mg of the agent administered per linear centimeter of wound or epithelial damage per 24 hours, although this figure may be modified upwards or downwards in response to the factors outlined above. The agent may preferably be provided in the form of a 1 pg/100 µL-1 mg/100 µL solution of the agent, and 100 µL of such a solution administered per linear centimeter of wound or epithelial damage over a 24 hour period.

The agent may more preferably be administered as a 10 pg/100 µL-100 µg/100 µL solution with 100 µL of such a solution administered per linear centimeter of wound or epithelial damage over a 24 hour period.

Most preferably the agent may be administered as a 1 ng/100 µL-1000 ng/100 µL solution with 100 µL of such a solution administered per linear centimeter of wound or epithelial damage over a 24 hour period.

Generally, compositions comprising agents of the invention should be formulated such that when administered to a wound a concentration of the agent of between 0.79 pM and 0.79 mM per linear centimeter of wound or epithelial damage is achieved. Preferably the agent may be provided at concentrations of between 7.9 pM and 0.079 mM per linear centimeter.

An agent of the invention (such as the peptides of Sequence ID Nos. 3 to 8) may be administered at a concentration of between 0.79 pM and 0.79 mM. Preferably an agent of the invention may be administered at a concentration of between 7.9 pM and 0.079 mM. Most preferably an agent of the invention may be administered at a concentration of between 0.79 nM and 0.79 µM.

Purely by way of example an injectable solution containing between 10 pg/100 µL and 100 µg/100 µL of an agent of the invention (such as a TGF-β3 of Sequence ID Nos. 3, 5, 7, 9 or 11) is suitable for application to promote accelerated dermal wound healing and/or inhibition of scarring when administered as an intradermal injection and dosed with 100 µL per linear cm of wound margin.

In the case of a TGF-β3 of Sequence ID No. 3, preferred dosages for administration to a wound may be in the region of 1 ng/100 µL-1000 ng/100 µL, and 100 µL of such a solution administered per linear cm of wound margin.

In the case of a TGF-β3 of Sequence ID No. 5, preferred dosages for administration to a wound may be in the region of 1 ng/100 µL-1000 ng/100 µL, and 100 µL of such a solution administered per linear cm of wound margin.

In the case of a TGF-β3 of Sequence ID No. 7, preferred dosages for administration to a wound may be in the region of 1 ng/100 µL-1000 ng/100 µL, and 100 µL of such a solution administered per linear cm of wound margin.

In the case of a TGF-β3 of Sequence ID No. 9, preferred dosages for administration to a wound may be in the region of 1 ng/100 µL-1000 ng/100 µL, and 100 µL of such a solution administered per linear cm of wound margin.

In the case of a TGF-β3 of Sequence ID No. 11, preferred dosages for administration to a wound may be in the region of 1 ng/100 µL-1000 ng/100 µL, and 100 µL of such a solution administered per linear cm of wound margin.

Agents of the invention may be used to promote accelerated wound healing and/or prevent, reduce or inhibit scarring as a monotherapy (e.g. through use of medicaments of the invention alone). Alternatively the methods or medicaments of the invention may be used in combination with other compounds or treatments for the promotion of wound healing or scar inhibition. Suitable treatments that may be used as parts of such combination therapies will be well known to those skilled in the art.

The inventors have found that TGF-β3s in accordance with the present invention may be advantageously formulated in the presence of a sugar. This sugar may be a reducing or non-reducing sugar and/or a phosphate or phosphonate derivative thereof. Examples of such sugars may be selected from, but are not limited to, those selected from the group consisting of maltose, mannose, trehalose, arabinose, mannitol, sucrose, fructose, dextrose and glucose. Preferred sugars may be selected from the group consisting of maltose and trehalose.

It will be appreciated that peptides comprising TGF-β3s of the invention may represent favourable agents to be administered by techniques involving cellular expression of nucleic acid sequences encoding such molecules. Such methods of cellular expression are particularly suitable for medical use in which the therapeutic effects of the peptides are required over a prolonged period, for example in contexts where it is desirable to augment over a period of time an otherwise defective wound healing response. It is particularly preferred that TGF-β3s to be administered via cellular expression comprise those peptides defined by Sequence ID Nos. 3, 5, 7, 9 or 11, or fragments or derivatives thereof. Nucleic acids encoding these peptides are set out in Sequence ID Nos. 4, 6, 8, 10 or 12.

Many known methods of administering peptide agents of the invention to tissues such as wounds have the disadvantage that it can be difficult to achieve sustained levels of the agent of the invention at the treatment site over the course of even a few days because the peptide agents may have short half-lives in vivo. The half-lives of the agents may be short for a number of reasons, which include:

(i) Degradation by proteases and the like.
(ii) Clearance by binding proteins.
(iii) Binding and inhibition of agent activity by extracellular matrix molecules.

Furthermore, agents used to promote accelerated wound healing and/or prevention, reduction or inhibition of scarring need to be administered in a suitable vehicle and are often provided as a composition comprising the agent and the vehicle. As discussed, such vehicles are preferably non-inflammatory, biocompatible, bioresorbable and must not degrade or inactivate the agent (in storage or in use). However, it can often be difficult to provide a satisfactory vehicle for delivering agents to a tissue with a wound to be treated.

A convenient way in which these problems can be obviated or mitigated is to provide a therapeutically effective amount of an agent of the invention at an area to be treated by means of gene therapy.

According to a fourth aspect of the present invention there is provided a delivery system for use in a gene therapy technique, said delivery system comprising a DNA molecule encoding a peptide selected from the group consisting of those defined by Sequence ID No. 3, Sequence ID No. 5, Sequence ID No. 7, Sequence ID No. 9 and Sequence ID No. 11, said DNA molecule being capable of being transcribed to lead to the expression of the chosen peptide.

According to a fifth aspect of the present invention there is provided the use of a delivery system as defined in the preceding paragraph for use in the manufacture of a medicament for use in the promotion of accelerated wound healing and/or prevention, reduction or inhibition of scarring.

In a sixth aspect of the present invention there is provided the use of a delivery system as defined in above for use in the manufacture of a medicament for use in the promotion of epithelial regeneration.

According to a seventh aspect of the present invention there is provided a method of promoting accelerated wound healing and/or prevention, reduction or inhibition of scarring, the method comprising administering to a patient in need of such treatment a therapeutically effective amount of a delivery system as defined for the ninth aspect of the invention.

According to an eighth aspect of the present invention there is provided a method of promoting epithelial regeneration, the method comprising administering to a patient in need of such treatment a therapeutically effective amount of a delivery system as defined for the ninth aspect of the invention.

Due to the degeneracy of the genetic code, it is clear that nucleic acid sequences encoding agents suitable for use in accordance with the invention may be varied or changed without substantially affecting the sequence of the product encoded thereby, to provide a functional variant thereof. The sequences of possible nucleic acids that may be used to encode peptides defined by Sequence ID Nos. 3, 5, 7, 9 or 11 will be readily apparent to the skilled person, and the skilled person will be able to make reference to the examples provided as Sequence ID Nos. 4, 6, 8, 10 or 12 respectively.

The delivery systems according to the invention are highly suitable for achieving sustained levels of an agent of the invention at a wound over a longer period of time than is possible for most conventional delivery systems. Agents of the invention suitable for promoting accelerated wound healing and/or inhibited scarring may be continuously expressed from cells at a wound site that have been transformed with the DNA molecule disclosed in the fourth aspect of the invention. Therefore, even if the agent of the invention has a very short half-life in vivo, therapeutically effective amounts of the agent may be continuously expressed from the treated tissue.

Furthermore, the delivery system of the invention may be used to provide the DNA molecule (and thereby the agent of the invention) without the need to use conventional pharmaceutical vehicles such as those required in ointments or creams that are contacted with the wound.

The delivery system of the present invention is preferably such that the DNA molecule is capable of being expressed (when the delivery system is administered to a patient) to produce a peptide defined by the group consisting of Sequence ID Nos. 3, 5, 7, 9 or 11, or a fragment or derivative of such a peptide. The DNA molecule may be contained within a suitable vector to form a recombinant vector. The vector may for example be a plasmid, cosmid or phage. Such recombinant vectors are highly useful in the delivery systems of the invention for transforming cells with the DNA molecule.

Recombinant vectors may also include other functional elements. For instance, recombinant vectors may be designed such that the vector will autonomously replicate in the nucleus of the cell. In this case, elements which induce DNA replication may be required in the recombinant vector. Alternatively the recombinant vector may be designed such that the vector and recombinant DNA molecule integrates into the genome of a cell. In this case DNA sequences which favour targeted integration (e.g. by homologous recombination) are desirable. Recombinant vectors may also have DNA coding for genes that may be used as selectable markers in the cloning process.

The recombinant vector may also further comprise a promoter or regulator to control expression of the gene as required.

The DNA molecule may (but not necessarily) be one that becomes incorporated in the DNA of cells of the subject being treated. Undifferentiated cells may be stably transformed leading to the production of genetically modified daughter cells. When this is the case, regulation of expression in the subject may be required e.g. with specific transcription factors, gene activators or more preferably with inducible promoters which transcribe the gene in response to a signal specifically found at a wound. Alternatively, the delivery system may be designed to favour unstable or transient transformation of differentiated cells in the subject being treated. In this instance, regulation of expression may be less important because expression of the DNA molecule will stop when the transformed cells die or stop expressing the protein (ideally when the promotion of accelerated wound healing with reduced scarring has been effected).

The delivery system may provide the DNA molecule to a subject without it being incorporated in a vector. For instance, the DNA molecule may be incorporated within a liposome or virus particle. Alternatively the "naked" DNA molecule may be inserted into a subject's cells by a suitable means e.g. direct endocytotic uptake.

The DNA molecule may be transferred to the cells of a subject to be treated by transfection, infection, microinjection, cell fusion, protoplast fusion or ballistic bombardment. For example, transfer may be by ballistic transfection with coated gold particles, liposomes containing the DNA molecule, viral vectors (e.g. adenovirus) and means of providing direct DNA uptake (e.g. endocytosis) by application of plasmid DNA directly to a wound topically or by injection.

Cellular expression of the agent of the invention may be by cells at the edge of the undamaged area surrounding the wound, or may alternatively be by cells therapeutically introduced into the wound (for example cultured endogenous or exogenous cells involved in the wound healing response).

It will be appreciated that cells that are to be introduced therapeutically to promote accelerated wound healing and/or prevention, reduction or inhibition of scarring may be manipulated ex vivo such that they express increased levels of an agent of the invention, and then introduced into the wounded area. Such cells may preferably be cells cultured ex vivo for use in the preparation or manufacture of artificial skin or skin substitutes to be used in the promotion of wound healing. The cells may more preferably be autologous cells, although it will be appreciated that any suitable cells may be used.

Accordingly, in a ninth aspect of the invention, there is provided a medicament comprising cells induced to express an agent of the present invention.

The induction of cellular expression of an agent of the invention may be effected by means of the incorporation in the cells of nucleic acids causing the expression of agents suitable for use in accordance with the invention.

The invention will now be further described by way of example with reference to the following experimental protocols and studies, and the accompanying Figures in which:

Table 1 shows values indicative of amino acid residues' propensity for involvement in alpha-helix formation;

Table 2 sets out details of nomenclature used in reference to mutant TGF-β3s of the invention;

Table 3 sets out re-folding efficiency of wild-type TGF-β3 and TGF-β3s of the invention;

Table 4 compares the biological activity of wild type TGF-β3 and Gly63-Ala (a TGF-β3 protein of the invention) as assessed by cell growth inhibition assay;

Table 5 sets out concentrations of reagents used in in vivo wound healing studies;

Table 6 sets out concentrations of reagents used in in vivo wound healing studies;

FIG. 1 shows a chromatogram of TGF-Beta 3 'Wild-Type' on a Phenyl-Sepharose Column;

FIG. 2 shows a chromatogram of TGF-Beta 3 'Wild-Type' Monomer and Dimer on UNO-S1 Column;

FIG. 3 shows a comparison of TGF-Beta 3 Mutant Proteins and 'Wild-Type' TGF-Beta 3 by SDS-PAGE stained with Coomassie Blue (please note that the buffer exchange of Gly63-Ala and Gly63-Pro mutant proteins resulted in some sample loss therefore the actual concentration added to the gel were rather less than the 3 μg stated);

FIG. 4 shows the template used for excisional wounding;

FIG. 5 shows day 3 average macroscopic assessment scores for incisional wounds (A and B) treated with wild type TGF-Beta 3 or TGF-β3s of the invention, where "*" indicates significantly increased healing compared to naïve wounds ($p<0.05$);

FIG. 6 Day 3 microscopic average wound width for excisional wounds (C and D) Treated with 'wild-type' and mutant TGF-Beta 3 proteins;

FIG. 7 shows the template used for incisional wounding;

FIG. 8 illustrates macroscopic scar scores (day 70) for wounds treated with 'wild-type' TGF-Beta 3, Gly63-Ala and Gly63-Pro;

FIG. 9A and 9B illustrate macroscopic scar images (day 70) for wounds treated with 'Wild-type' TGF-Beta 3, Gly63-Ala and Gly63-Pro;

FIG. 10 illustrates macroscopic scar scores (day 70) for wounds treated with 'Wild-type' TGF-Beta 3, Glu12-Ser and double Serine mutant (Glu12-Ser & Arg52-ser), where "+" indicates significantly decreased scarring compared to placebo treated wounds ($p<0.05$);

FIG. 11A and 11B illustrate macroscopic scar images (day 70) for wounds treated with 'Wild-type' TGF-Beta 3, Glu12-Ser and double Serine mutant (Glu12-Ser & Arg52-Ser);

FIG. 12A and 12B illustrate representative microscopic scar images of wounds treated with 'Wild-type' TGF-Beta 3, Gly63-Pro and Gly63-Ala Mutant Proteins (70 days Post-Wounding); and FIG. 13A and 13B illustrate representative microscopic scar images of wounds treated with Glu12-Ser and Double Serine mutant (Glu12-Ser and Arg 52-Ser) after 70 days Post-Wounding).

Details of sequences of particular interest are provided in the section "Sequence Information".

Experimental Protocols and Results

1 Generation, Production, Refolding, and Purification of TGF-β3s According to the First and Second Aspects of the Invention.

1.1 Generation of cDNA

Total RNA from a human incisional wound (taken day 5 post-wounding) was treated with DNA-Free (Ambion) to remove any contaminating DNA. Using total RNA as a template, TGFBeta-3 cDNA was generated by Reverse Transciptase-Polymerase Chain Reaction (RT-PCR). The RT-PCR master mix was prepared from Brilliant® QRT-PCR Core Reagent Kit, 1-Step (Stratagene). One microgram of RNA was added to 50 μL of a solution containing: One-step QRT-PCR buffer, 0.2 mM dNTPs, 3.5 mM $MgCl_2$, 1 μL StrataScript reverse transcriptase, Taq Polymerse 2.5 units, 0.4 μM Sense primer (5' GAT ATA CCA TGG CTT TGG ACA CCA ATT ACT ACT GC 3'), 0.4 μM Sense primer (5'-CAG CCG CGA TCC GTC GAC TCA GCT ACA TTT ACA AGA C 3'). The reaction was placed in a thermal cycler (Hybaid PCR Expresses) and run under the following conditions: 30 min at 45° C., 10 min at 95° C., then 40 cycles of 95° C. for 30 sec, 65° C. for 1 min and 72° C. for 1 min. Final step of 72° C. for 10 min. PCR samples were run on 2% (w/w) agarose gel to verify band size and purified using Wizard PCR Prep Kit (Promega).

1.2 Construction of Plasmid

The pET-3d vector is derived from pBR322 vector and contains a T7 promoter under LacUV5 control and an Ampicillin resistant marker gene. The TGF-Beta 3 cDNA fragments (generated in Section 3.2) were sub-cloned into pET-3d at the Nco I and Bam HI sites (5'-3' respectively). The resulting ligation was then transformed into XL10 Gold cells (Stratagene) and colony PCR analysis was performed to locate clones containing an insert. The final clone was grown up and plasmid DNA extracted into water using Qiaprep®Spin Miniprep Kit (Qiagen). The plasmid was sequenced and verified using a T7 promoter primer (5'-TAA TAC GAC TCA CTA TAG GG-3') and a T7 terminator primer (5'-GCT AGT TAT TGC TCA GCG G-3').

1.3 Site Directed Mutagenesis

The 'wild-type' TGF-Beta 3 construct from Section 1.2 underwent site directed mutagenesis to generate two mutated constructs encoding for TGF-Beta 3 mutant proteins. The construct/mutant nomenclature and nucleotide sequence change are summarised in Table 2. The nucleotide positions that underwent mutagenesis are shown in the Sequence Information section.

The In-vitro site-directed mutagenesis methodology was based on Stratagene's Quick Change® Site directed Mutagenesis kit. 100 ng of plasmid (from Section 1.2) was added to a solution containing: 2.5 μL 10× Quick Change® Multi Reaction Buffer, Quick solution, 100 ng of Mutagenic Primer, 1 mL dNTP mix, Pfu Turbo DNA Polymerase (Stratagene), made up to a final volume of 2.5 mL with double distilled water. The reaction was placed in a thermal cycler (Hybaid PCR Expresses) and run under the following conditions: 1 min at 95° C., 30 cycles of 1 min at 95° C., 55° C. for 1 min and a final step of 65° C. for 2 min. Once the thermal cycling was complete the reactions were placed on ice for 2 min to reduce the temperature below 37° C. 1 μL of DpnI restriction enzyme (10 U/μL) was added to each reaction and mixed thoroughly. The reaction mixture was centrifuged (1 min 10,000 rpm in a Sorvall Biofuge) then incubated at 37° C. to digest the parental ds-DNA. 1-5 µL of DpnI-treated DNA from each mutagenesis reaction was added 45 uL of resuscitated XLI-Blue *E. coli* (Stratagene) and 2 µL β-ME mix (Stratagene). The suspension was mixed and incubated on ice for 30 minutes. The suspension was heated to 42° C. in a water bath for 30 seconds. The mixture was incubated on ice for a further 2 min. 0.5 mL of pre-heated (42° C.) NZY+ broth was added to each cell suspension. The transformation broth was incubated for 1 hour with shaking at 225-250 rpm. 1 µL, 10 µL and 100 µL of the transformation broth from each mutagenesis reaction was spread onto LB agar plates containing 100 µg/mL of Ampicillin (Sigma), 80 µg/ml of 5-bromo-4-chloro-3-inodlyl-β-D-galactopyranoside (X-gal, Stratagene), 20 mM of Isopropyl β-D-Thiogalctopyranoside (IPTG, Sigma) and incubated for 18 hours at 37° C. The blue colonies contained the mutated plasmid. A single colony from each mutant type was picked off the agar and used to inoculate 10 mL of LB medium containing 100 µg/mL Ampicillin. The plasmid was isolated using QIAprep® Spin Miniprep Kit (Qiagen). The plasmids were sequenced and verified for correct mutation using pQE for and pQE Rev primers.

1.4 Transformation and Cloning

10 µL (50 ng per µl) of plasmid DNA (from Section 1.2 and 1.3) was added to 1 mL of cold (4° C.) competent *E. coli* BL21 (DE3) pLysS Singles™ cells (Novagen). After 20 min the cells were heat shocked by incubation for 30 sec at 42° C. in a water bath. 100 µL of Psi medium was added to the cell/plasmid mixture and shaken at 37° C. for 90 min. 50 µl and 100 µl aliquots were plated onto LB agar plates containing 100 µg/mL Ampicillin (Sigma) and incubated for 18 hours at 37° C. Single colonies were cultivated and frozen cell stocks generated and stored at −80° C. Plasmid DNA was analysed from cells stocks to verify correct transformation.

1.5 Expression

An ampoule of frozen transformed *E. coli* cells (from Section 1.4) were recovered and inoculated into a baffled Erlenmeyer flask, containing 100 mL of LB media and 100 µg/mL of Ampicillin. The flask was incubated with shaking, overnight at 37° C. 5 mL of this overnight culture were added to 2-liter Erlenmeyer flask (500 mL of LB media/and 100 µg/mL of Ampicillin) and incubated with shaking at 37° C. 2 mL Broth samples were taken hourly to track growth and TGF-Beta 3 'wild-type' and mutant protein expression (post-induction). Growth was determined by measuring absorbance on a spectrophotometer, at a wavelength of 600 nm. When the absorbance measured 0.6 Abs the cells were induced to express 'wild-type' and mutant TGF-Beta 3 proteins by the addition of Isopropyl β-D-Thiogalactopyranoside (IPTG, Sigma) to a final concentration of 1 mM. The cultures were incubated for an additional 4 hours. 0.5 mL of broth samples were pelleted by centrifugation (10 min 10,000 rpm in a Sorvall Biofuge) and the supernatant discarded. The pellet was re-suspended in 50 µL of Sodium Dodecyl Sulfate (SDS)-polyacrylamide gel-electrophoresis (PAGE) sample buffer and heated for 10 minutes in a water bath at 95° C. 10 µL samples were loaded onto SDS-PAGE. SDS-PAGE and Coomassie Blue staining was performed as described in A. T Andrews (1986), using a Hoefer®Mighty Small SE 245 Dual Gel Caster (Amersham). The gels were 1 mm thick and contained 15% (v/v) polyacrylamide gel.

1.6 Cell Harvesting and Isolation of Inclusion Bodies

Cells from Section 1.5 were pelleted by centrifuging at 5000 g for 10 min in a Hettich Rotina 46R centrifuge with a 4315 Rotor. Cell disruption and recovery of insoluble (inclusion bodies) TGF-Beta 3 protein was performed at 4° C. The cells were suspended in 50 mL of 100 mM Tris/HCl (Sigma), 10 mM EDTA (Sigma) pH 8.3 and were disrupted by sonication using a Sanjo Soniprep 150. 0.2% (w/w) Triton X-100 (Sigma) was added and the suspension and stirred for one hour. The suspension was centrifuged at 15,000 g for 40 min. The pellet was re-suspended in 50 mL of 100 mM Tris/HCl, 10 mM EDTA pH 8.3 before being centrifuged for 40 minutes at 12,000 g.

1.7 Solubilisation of Inclusion Bodies

The sediment from Section 1.6 was re-suspended in 40 mL of 8M Urea 1% (w/w) DL-Dithiothreitol (DTT) and disrupted in a Heidolph Diax 900 homogeniser. The suspension was covered and left stirring for 1 hour to solubilise the inclusion bodies and reduce TGF-Beta 3 'wild-type' and mutant proteins to their monomeric form. The suspension was then centrifuged for 30 minutes at 15,000 g. The supernatant was dialysed to exchange buffer from 8 M Urea (ICN Biomedical) to 10% (v/v) acetic acid. The *E. coli* proteins that were soluble in the 8 M urea precipitate out of solution when the buffer is exchanged to 10% (v/v) acetic acid. 1% (w/w) DTT (Sigma) was added to the suspension, covered and left stirring for 30 min to reduce any disulfide bonds that may have formed between TGF-β3 monomers during the buffer exchange. The suspension was centrifuged at 12,000 g for 40 min to separate the soluble and non-soluble proteins. Samples were taken from urea solubilisation and buffer exchange steps (acetic acid soluble and non-soluble material), and then analysed using SDS-PAGE.

1.8 Ultrafiltration

The 10% (v/v) acetic acid soluble material from Section 1.7 underwent ultrafiltration using a 10 kDa membrane on a Vivoflow50 (Vivascience). The purpose of this was to reduce the volume of 10% (v/v) acetic acid suspension to 3 mL and to remove low molecular weight proteins (<10 kDa).

1.9 Gel Filtration

The sample from Section 1.7 was chromatographed on a Hiprep 26/60 Sephacryl S-100 high-resolution column (Amersham, 320 mL) in 10% (v/v) acetic acid at a flow rate of 1.5 mL/min. Fractions containing monomeric denatured TGF-Beta 3 (which eluted between 100 min and 140 min) were pooled.

1.10 Lyophilisation

The pooled fractions containing denatured monomeric TGF-Beta 3 were lyophilised using a IEC Lyoprep-3000 freeze dryer to remove acetic acid and water from the sample.

1.11 Refolding

The lyophilised, monomeric, TGF-Beta 3 from Section 1.10 was solubilised in 8 M urea containing 10 mM DTT until a final TGF-Beta 3 concentration of 10 mg/mL was achieved. The TGF-Beta 3 solution was added dropwise, while stirring to re-folding solution (1 M 3-(-Pylidino)-1-propane Sulfonate (NDSB-201), 20% (v/v) Dimethyl Sulfoxide (DMSO, Sigma), 2% (w/v) 3-(3-cholamidopropyl) dimethylammonio-1-propanesulfonate (CHAPS), 1 M NaCl (Sigma), 1% (w/v) reduced Glutathione (GH, Sigma), 0.05 M Trizma®Base (Sigma) pH 9.3) until a final concentration of 0.2 mg/mL TGF-Beta 3 was achieved. It is important the pH is kept within a range of 9.2-9.4 using concentrated NaOH/HCl. The solution was covered with Parafilm, which was punctured to allow oxidation of the monomeric TGF-Beta 3 and left stirring at 8° C. After 144 hours the solution was centrifuged at 15,000 g for 40 minutes to remove the precipitate formed and the pH was adjusted to pH 3.5 with glacial acetic acid. The supernatant contained disulfide linked dimeric TGF-Beta 3, which was determined by SDS-PAGE (non-reduced) and Western Blotting. The SDS-PAGE was carried out as described in section 2.1.

For the Western Blotting, samples were loaded onto a 1 mm thick, 15% (v/v) polyacrylamide gel. Once electrophoresis was completed the proteins within the gel were then electrophoretically transferred on to nitrocellulose paper (Sigma) using TE22 Western-Blotting Apparatus (Pharmacia), as outlined in the instruction manual. Non-specific binding sites on the nitrocellulose were then blocked with blocking buffer (5% (w/v) Skimmed milk powder, 1% (v/v) Polyoxyethylenesorbitan Monolaurate (Tween 20, Sigma) in Phosphate Buffered Saline (Invitrogen)). The nitrocellulose was then washed in washing buffer (PBS, 0.1% Tween 20). The nitrocellulose was then incubated for 1 hr with the primary antibody (MAB643 (R&D systems)) diluted 1:500 with 0.1% (v/v) Tween 20 in PBS. The nitrocellulose was again washed before incubation for 1 hr with the secondary antibody goat anti-mouse antibody (Abcam) diluted 1:3000 with 0.1% (v/v) Tween 20 in PBS. The nitrocellulose received a final wash before the addition ECL reagent (Amersham) to visualise the antigen-antibody complexes. In a dark room X-ray film was exposed to the nitrocellulose before being immersed in developer, fix and stop solutions. The nitrocellulose was then left to dry. The re-folding the TGF-Beta 3 'wild-type' and mutant monomeric proteins showed varying levels of dimer formation. The percentage recovery of correctly re-folded dimer from other incorrectly re-folded or non-dimeric TGF-Beta 3 proteins are shown in Table 3.

Interestingly the amino acid substitutions within the alpha helix of the TGF-Beta 3 proteins that caused greatest impact on re-fold yield (dimer formation). Stabilisation of the alpha helix by substituting Glycine with Arginine increased re-fold yields from 20% to 50%. Conversely disruption of the alpha helix by substituting Glycine with Proline resulted in a much lower percentage of dimer formation. This indicates that the alpha helix plays an important role in the correct re-folding of the TGF-Beta 3 molecule. Substituting the amino acids involved in the formation of the 'salt-bridge' did not effect re-fold yields.

1.12 Hydrophobic Interaction Chromatography

The renaturation solution from Section 1.11 was concentrated to 50 mL by Ultrafiltration with a 10 kDa (molecular weight cut off) membrane on a Vivoflow50 (Vivascience). The renaturation solution was diluted 1:1 with a solution containing 2 M Ammonium Sulphate (Sigma) and 10% (v/v) acetic acid. A 2 ml Biorad column filled with the Phenyl-Sepharose Flast Flow (Amersham) was equilibrated with buffer A (1.0 M Ammonium sulphate and 10% (v/v) Acetic acid). 20 mL of the diluted renaturation solution was applied to this column at a flow rate of 1 mL/min (this flow rate was used through out the procedure). The column was then washed in buffer A until the absorbance reading at 280 nm reached baseline level (10 mL). 100% Buffer B (10% (v/v) acetic acid 30% (v/v) Isopropanol) was applied to the column. The first peak, which contains TGF-Beta 3 proteins in both monomeric and dimeric forms, was pooled (see FIG. 1).

1.13 Cation Exchange Chromatography

Cation exchange chromatography was used to isolate the dimeric TGF-Beta 3 proteins from the monomers. A 2 mL UNO-S1 Column (Biorad) was equilibrated with buffer A containing 10% (v/v), acetic acid, 30% (v/v) Isopropanol). The pooled fractions from Section 3.12 were applied at flow rate of 1 mL/min onto the UNO-S1 column. The column was then washed in buffer A until the absorbance reading at 280 nm reached baseline level (5 min). A linear gradient was run over 5 mins ending with a mixture of 60% Buffer A and 40% Buffer B (10% (v/v) acetic acid, 30% (v/v) Isopropanol and 1 M NaCl). The application of this buffer mixture was maintained for a further 15 minutes. Monomeric TGF-Beta 3 was eluted from the column after 10 min following sample injection. A second linear gradient was applied over 5 minutes ending with 100% Buffer B and maintained for a 10 minutes. Dimeric TGF-Beta 3 was eluted from the column 30 mins after sample injection (see FIG. 2).

1.14 Ultrafiltration/Diafiltration

The fractions containing purified monomeric and dimeric TGF-Beta 3 molecules from Section 1.13 underwent ultra filtration/diafiltration to exchange the buffer to 20 mM Acetic Acid, 20% (v/v) Isopropanol and concentrate the sample to ~10 mg/mL (TGF-Beta 3 concentration was determined by U.V spectrometry). A Vivoflow50 (Vivascience) with a 10 kDa cut off was used exchange buffer and concentrate the samples.

2 In Vitro Characterisation of TGF-β3s of the Invention.

2.1 SDS-PAGE Analysis of Purified TGF-β3s of the Invention

The purified TGF-Beta 3 mutant proteins (from Section 1.14) were assessed by SDS-PAGE to determine purity and molecular weight. Due to the low pH in the TGF-Beta 3 mutant samples from Section 3.14 the buffer was exchanged using protein desalting spin columns (Pierce) into SDS-PAGE sample buffer. 3 μg of purified TGF-Beta 3 mutant proteins (reduced and non-reduced samples), 3 μg 'wild-type' TGF-Beta 3 positive control (reduced and non-reduced) and 10 μL Invitrogen Mark 12 molecular weight standards were loaded onto a polyacrylamide gel (10%-20% (v/v) gradient of Acrylamide). Once the electrophoresis was complete the gel was stained with Coomassie Blue.

As expected the 'wild-type' TGF-Beta 3 and the Gly63-Ala mutant protein ran to identical positions on the gel (~13 kDa for reduced and 25 kDa for the non-reduced samples). Interestingly no Gly63-Pro mutant protein bands were detected on the non-reduced gel but were detected on reduced gel. As the re-fold efficiency of Gly63-Pro was very low (<1%) it is likely multiple re-fold species were produced, which were below the levels detectable by Coomassie (>1 μg). However when these species were reduced the concentration of the reduced Gly63-Pro monomer was above the 1 g Coomassie stain detection limit and therefore Gly63-Pro could be seen on the reduced gel. The reduced Gly63-Pro protein band position was slightly higher than the band for 'wild-type' TGF-Beta 3. This was to be expected as the substitution of Glycine 63 for a Proline made the Gly63-Pro mutant protein a larger molecule than 'wild-type' TGF-Beta 3 (see FIG. 3).

2.2 Cell Growth Inhibition Assay to Compare the Biological Activity of TGF-β3s of the Invention with that of Wild Type TGF-β3

The cell growth inhibition assay (A Meager, 1991) is an in-vitro biological activity test for TGF-Beta molecules. The colorimetrical assay is based on the inhibitory effect of TGF-Beta molecules on the growth of Mink Lung Epithelial cells (MLEC). 100 μL of cell suspension containing: $1\times10^4$ MLEC cells/mL and complete medium (DMEM (Invitrogen), 0.01 M Hepes buffer (Invitrogen), 2 mM L-Glutamine (Invitrogen), L-Arginine (Invitrogen), L-Asparagine (Invitrogen), 100 units/mL Penicillin (Invitrogen), 50 μg/mL Streptomycin (Invitrogen) and 5% Foetal Calf Serum (Invitrogen)) was added to each well of a 96 well tissue culture plate. After overnight incubation at 37° C., 5% $CO_2$, 100 μL of serially diluted (10 pg/mL to 500 pg/mL) dimeric TGF-Beta 3 mutant samples (from Section 3.14) were added to the plate(s). Control wells received 200 μL of complete medium and 10% (v/v) 0.25 M Maltose. The plates were incubated for a further 120 hr and 50 μL of 2 mg/mL, 3-[4,5-dimethylthiazonl-2-yl]-2,5-diphenyltetrazolium bromide: thiazolyl blue (MTT; Sigma) was added to each well. The plates were incubated for an additional 4 hours and media was then removed. 100 μL of 0.05 M HCl (BDH), absolute Isopropanol (BDH) was added to each well and the resultant solubilised formazan was quantified at 570 nm using a microplate reader (Victor$^2$ 1420).

Gly63-Ala, a TGF-β3 of the invention, had an inhibitory effect on MLEC cells over a concentration range of 0-500 pg/mL. As can be seen from Table 4, Gly63-Ala mutant protein had an $IC_{50}$ of 34 pg/mL compared to 'wild type' TGF-Beta 3 having an $IC_{50}$ of 26 pg/mL.

2.3 Amino Acid Sequence Analysis

Fifty micro liters of purified 'wild-type' and mutant TGF-Beta 3 samples from Section 3.14 were vacuum dried and then re-suspended in 20 μL of a solution containing 50 mM $NH_4HCO_3$ and 10% (v/v) Acetonitile. 20 μg of sequencing grade Trypsin (Promega) was re-suspended in 10 μL of kit supplied re-suspension buffer (Promega) to give a Trypsin concentration of 2 μg/μL. This was then diluted into 50 mM 50 mM $NH_4HCO_3$ and 10% (v/v) Acetonitrile to give a final trypsin concentration of 0.2 μg/μL. The digestion was performed overnight by the addition of trypsin in a 1:20 (w/w) ratio with 'wild-type' and mutant TGF-Beta 3 proteins. The digestion was quenched by the addition of formic acid (Fluka) to a final concentration of 0.1% (v/v). The samples were then diluted to 1 pmole/μL. The peptides were then analysed by a process of nano-flow RPLC-MS (Ultimate system, Dionex online to a Q-ToF2, Micromass). The chromatography was performed on a 75 μm C18 column (LC packings) utilising a 45 min gradient from 5% (v/v) Acetonitrile to 55% (v/v) Acetonitrile. The MS analysis took the form of data dependent analysis where the instrument measured the m/z of peptide ions eluting from the LC and selecting appropriate ions for MS-MS analysis where collisionally induced decomposition was employed to fragment peptide ions to render sequence information.

3 In Vivo Characterisation of TGF-β3s of the Invention

The biological effects of re-folded active 'wild-type' and mutant TGF-Beta 3 proteins were investigated on incisional and excisional wound healing (3 days post-wounding) and scarring (70 days post-wounding) in adult, male rats.

3.1 Comparison of the Effects of Wild Type TGF-β3 and TGF-β3s of the Invention on Wound Healing Male rats (Sprague Dawley) are anaesthetized with Halothane and their backs shaved. Wounding positions were marked using a standard template with skin marking ink as shown in FIG. 4. Samples were diluted in sterile vehicle buffer containing 0.25 M Maltose (Sigma), 0.002% (v/v) acetic acid and 0.33% (v/v) Isopropyl Alcohol to concentrations described in Table 4. All samples were filter sterilised and endotoxin free. Four rats were used for each treatment group. 100 μL of sample from each treatment group (Table 4) was injected intra-dermally into marked wound positions A and B (except rats receiving no treatment (naïve)) At wound positions A and B punch biopsies were made. All animals were caged separately. After 24 hours the animals received a second dose of sample. After 3 days wounds were photographed and analysed using a macroscopic Visual Analogue Scoring system (modified from Beausang, E et al 1998). Statistical analysis of the data was performed using Mann Whitney U/Student T tests. A value of p<0.05 was considered significant.

3.2 Assessment of Day 3 Incisional Wounds Treated with Wild Type TGF-β3 or TGF-β3s of the Invention on Wound Healing Using a Macroscopic Visual Analogue Scale Incisional wounds were examined after 3 days using a macroscopic Visual Analogue Scale (VAS). On this ten-point scale a score of 0 represents a well-healed wound and a score of 10 represents a very poorly healed wound. Data shows that:

Treatment with 50 ng/100 μL or 100 ng/100 μL of wild-type TGF-Beta 3 decreases the VAS score (i.e., improves the macroscopic appearance of wounds) compared to no treatment (naïve control). Treatment with the 100 ng/100 μL dose significantly improved (p<0.05) the appearance of wounds compared to no treatment (naïve control) i.e., accelerated healing.

Treatment with 50 ng/100 μL or 100 ng/100 μL of the Gly63-Ala mutant decreases the VAS score compared to no treatment (naïve control) and are comparable to wounds treated with 'wild-type' TGF-Beta 3 i.e., did not impair healing.

Treatment with 50 ng/100 μL or 100 ng/100 μL of the Gly63-Pro mutant decreases the VAS score compared to no treatment (naïve control) and are comparable to wounds treated with 'wild-type' TGF-Beta 3 i.e., did not impair healing.

3.3 Microscopic Assessment of Wound Width for Day 3 Excisional Wounds Treated with Wild-Type and Mutant TGF-Beta 3 Proteins Excisional wound width was assessed microscopically after 3 days All wounds treated with TGF-Beta 3 'wild-type' and mutant proteins showed comparable wound width to the placebo and no treatment (naïve) controls, confirming that TGF-Beta 3 mutant proteins have no adverse effect on healing (FIG. 6).

3.4 The Effect of 'Wild-Type' and Mutant TGF-Beta 3 Proteins on Wound Scarring (Day 70 Wounding).

Male rats (Sprague Dawley) are anaesthetized with Halothane and their backs shaved. Wounding positions were marked using a standard template with skin marking ink as shown in FIG. 7. Samples were diluted in sterile vehicle buffer containing 0.25 M Maltose (Sigma), 0.002% (v/v) acetic acid and 0.33% (v/v) Isopropyl Alcohol to concentrations outlined in Table 5. All samples were sterile, endotoxin free, and pyrogen free. Four rats were used for each treatment group. 100 μL of sample from each treatment group (Table 6) was injected intra-dermally into marked wound positions A and B (except rats receiving no treatment (naïve)). At wound positions A and B full thickness 1 cm long incisions were made with a No. 11 scalpel blade. All animals were caged separately. After 24 hours the animals received a second dose of sample. After 70 days scars were photographed and analysed using a macroscopic Visual Analogue Scoring system (modified from Beausang, E et al 1998). The wounds were excised and placed into 10% Buffered saline before being processed into a wax block. The wax blocks were cut into 5 μM serial sections and placed on slides. The slides were stained with Massons Trichrome and analysed. Statistical analysis of the data was performed using Mann Whitney U/Student T tests. A value of p<0.05 was considered significant.

3.5 Assessment of Day 70 Incisional Wounds Using Macroscopic VAS.

Incisional wounds were examined after 70 days using a macroscopic VAS system. A score of 10 indicates a bad scar and a score of 0 is normal skin (FIG. 8). VAS analysis of the day 70 wounds shows that:

'Wild-type' TGF-Beta 3 (at 50 ng/100 μL and 100 ng/100 μL doses) reduced scarring compared to the placebo treated and naïve wounds. For both doses this reduction is statistically significant (p<0.05) compared to the placebo treated wounds.

Gly63-Ala mutant (at 50 ng/100 μL and 100 ng/100 μL doses) reduced scarring compared to the placebo treated and naïve wounds. For the 50 ng/100 µL dose this reduction is statistically significant (p<0.05) compared to the placebo treated wounds.

Gly63-Pro mutant (at 50 ng/100 µL and 100 ng/100 µL doses) reduced scarring compared to the placebo treated and naïve wounds.

Glu12-Ser mutant (at 50 ng/100 µL and 100 ng/100 µL doses) reduced scarring compared to the placebo treated and naïve wounds. For the 50 ng/100 µL dose this reduction is statistically significant (p<0.05) compared to the placebo treated wounds.

Double serine mutant (Glu12-Ser & Arg52-Ser) at 50 ng/100 µL and 100 ng/100 µL doses reduced scarring compared to the placebo treated and naïve wounds.

3.6 Microscopic Assessment of Day 70 Incisional Wounds.

The macroscopic effects noted using the VAS scoring system were confirmed by histological analysis. Representative examples of histological slides are shown in FIGS. 12 and 13. The histological photomicrographs show that addition of TGF-β3 proteins in accordance with the invention induces a similar improvement to that seen with "wild-type" TGF-β3. The proteins of the invention induce the collagen fibres within the scar to have similar morphology and organisation to those in the surrounding normal skin.

4 Conclusions

The flexibility of the alpha helix (between amino acid residues 58-67) impacts on the formation of functional, correctly re-folded, dimeric TGF-Beta 3 during re-folding. Stabilising the alpha helix by substituting Glycine-63 with Alanine greatly improves the re-fold efficiency where as destabilising the alpha helix by substituting Glycine-63 with Proline has the opposite effect.

Substituting the Glycine 63 with Alanine or Proline does not alter the wound healing compared to 'Wild-type' TGF-Beta 3.

Gly63-Ala and Gly63-Pro reduce scarring compared placebo treated and untreated wounds.

The formation of the 'Salt-Bridge' (between Arg52 and Glu12) does not alter the re-fold efficiency of TGF-Beta 3.

Glu12-Ser and double Serine Mutant reduces scarring compared placebo treated and untreated wounds.

5. Preferred Protocols for the Production of Monomeric or Dimeric TGF-#3s in Accordance with the Present Invention.

Preferred conditions for the generation of correctly refolded monomeric TGF-Beta 3s in accordance with the present invention are as follows:

0.7 M 2-(cylcohexylamino) ethanesulfonic acid (CHES), 2 mM reduced glutathione (GSH), 0.4 mM oxidised Glutathione (GSSG), 0.12 mg/mL TGF-Beta 3, pH 9.5 at 2-8° C.

30 mM Taurodeoxycholate, 0.7 M CHES, 2 mM GSH, 0.4 mM GSSG, 0.12 mg/mL TGF-Beta 3, pH 9.5 at 2-8° C.

1 M NDSB-201, 2 mM reduced glutathione (GSH), 2 mM oxidised Glutathione (GSSG), 0.12 mg/mL TGF-Beta 3, pH 9.5 at 2-8° C.

0.7 M CHES, 2 mM reduced glutathione (GSH), 2 mM oxidised Glutathione (GSSG), 0.12 mg/mL TGF-Beta 3, pH 9.5 at 2-8° C.

30 mM Taurodeoxycholate plus 1 M NDSB-221, 2 mM reduced glutathione (GSH), 2 mM oxidised Glutathione (GSSG), 0.12 mg/mL TGF-Beta 3, pH 9.5 at 2-8° C.

30 mM Taurodeoxycholate plus 0.7 M CHES, 2 mM reduced glutathione (GSH), 2 mM oxidised Glutathione (GSSG), 0.12 mg/mL TGF-Beta 3, pH 9.5 at 2-8° C.

30 mM Taurodeoxycholate, 0.7 M CHES, 2 mM GSH, 2 mM GSSG, 0.12 mg/mL TGF-Beta 3, pH 9.5 at 2-8° C.

In general a TGF-β3 in accordance with the present invention may be folded into a dimeric, biologically active form by a method comprising adding the solubilized, unfolded monomeric TGF-β3 to a solution containing:

(i) 2-(cylcohexylamino)-ethanesulfonic acid (CHES) or a functional analogue thereof; and (ii) a low molecular weight sulfhydryl/disulfide redox system; and incubating the growth factor in the solution until dimeric biologically active TGF-β3 is formed.

Preferred conditions for the generation of correctly refolded dimeric TGF-Beta 3s in accordance with the present invention are as follows:

0.7 M 2-(cylcohexylamino) ethanesulfonic acid (CHES), 2 mM reduced glutathione (GSH), 0.4 mM oxidised Glutathione (GSSG), 0.12 mg/mL TGF-Beta 3, pH 9.5 at 2-8° C.

30 mM Taurodeoxycholate, 0.7 M CHES, 2 mM GSH, 0.4 mM GSSG, 0.12 mg/mL TGF-Beta 3, pH 9.5 at 2-8° C.

30 mM Taurodeoxycholate, 0.7 M CHES, 2 mM GSH, 2 mM GSSG, 0.12 mg/mL TGF-Beta 3, pH 9.5 at 2-8° C.

Preferred Experimental Conditions:

5.1 Vector Cloning and Host Cell Transformation.

The pET-24d vector is derived from pBR322 vector and contains a T7 promoter under LacUV5 control and a kanamycin resistant marker gene.

DNA encoding TGF-β3s of the invention may be digested with 0.75 µL of NcoI (New England Biolabs) and 0.75 µL of BamH1 (New England Biolabs) with 1×BamH1 Buffer (New England Biolabs) in a 15 µL reaction (Nuclease Free Water, Novagen) at 37° C. for 4 hours. One microliter of pET-24d plasmid (Novagen) may be digested in the same manner. The digested cDNA and the large plasmid fragment are agarose gel purified and recovered using the SpinPrep Gel DNA extraction kit (Novagen).

The purified cDNA and plasmid fragments are ligated using T4 ligase kit (Novagen). The ligated cDNA/plasmid is transformed into HMS174 (DE3) (Novagen HMS174 (DE3) transformation kit). The transformants were selected by plating on Luria broth (LB) agar plates containing 50 µg/mL kanamycin (Invitrogen). Suitable clones are selected for restriction digest and/or expression.

5.2 Clone Screening for Product Expression

Clones are grown in shake flask cultures of half strength 'Terrific Broth' (6 g/L phytone peptone (Becton Dickinson), 12 g/L yeast extract (Becton Dickinson), 2 g/L glycerol (JT Baker), 1.16 g/L potassium phosphate monobasic (JT Baker), 6.25 g/L potassium phosphate dibasic (JT Baker), QS to 1 Litre with distilled water) and induced in exponential phase at $OD_{600}$ between 0.65 and 0.85 with 1 mM isopropyl beta-D-thiogalactopyranoside (IPTG). Post-induction samples are taken 3 hours after the addition of IPTG and analysed by sodium dodecylsulfate polyacrylamide gel electrophoresis (SDS-PAGE) for product induction and expression. Samples from suitable clones run on NuPAGE® Novex 12% Bis-Tris Gel, 1.0 mm (Invitrogen) for approximately 40-50 minutes at 120 milliAmps and 200 Volts and then stained with Coomassie Blue. Expression of TGF-β3s in accordance with the invention may thus be induced in these cultures.

5.3 Frozen Cell Stock

Clones are grown in shake flasks in half strength Terrific Broth to an $OD_{600}$ of approximately 1. and stored as glycerol stocks by the addition of glycerol to 20% (v/v). 1.2 mL of broth was aliquoted into 12×2 mL cryovials (which contained 0.3 mL of glycerol) and then stored at −70° C.

5.4 Sequence Confirmation of TGF-Beta 3 Gene.

Samples of cultures used for frozen cell stocks are taken before the addition of glycerol and used for plasmid isolation using a Qiagen MiniPrep Kit. The isolated plasmid is sequenced and verified using a T7 promoter primer (5'-TAA TAC GAC TCA CTA TAG GG-3') and a T7 terminator primer (5'-GCT AGT TAT TGC TCA GCG G-3').

5.5 Seed Culture.

A selected suitable clone is inoculated into a 2 Litre baffled Erlenmeyer flask, containing 500 mL of HySoy medium (12 g/L Hy-Soy (Quest International), 24 g/L yeast extract (Becton Dickinson), 10 g/L NaCl (Sigma) and 10 g/L glycerol (Sigma) and 50 µg/mL of kanamycin. The flask is incubated with shaking at 37° C. and 200 rpm and sampled periodically to measure $OD_{550}$. When the OD of the culture reaches 3.21 U/mL (after 7 hours) the cell broth is used to seed a 150 L fermenter (100 L working volume).

5.6 Fermentation

Nine hundred milliliters of cell broth (from Section 3.6) is used to inoculate a 150 L fermenter (WHE) containing 90 L of Batch Culture Media (0.6 g/L $K_2HPO_4$, 0.4 g/L $KH_2PO_4$, 1.25 g/L $NH_4SO_4$, 12 g/L HY-Soy, 24 g/L yeast extract and 10 g/L glycerol). The fermentation operating parameters are controlled as follows: temperature set point, 37° C.; pH set point, 7.0 (maintained using 4 N ammonium hydroxide and 4 N phosphoric acid), and; dissolved oxygen (DO) initially calibrated to 100%. The vessel head pressure was 7 psi, and the agitation and airflow were 200-400 rpm with one volume of air per volume of medium per minute (vvm or slpm), respectively. DO is maintained above 20% by adjusting the fermentation set point parameters in the following priority: Agitation (max 400 rpm), aeration (max 1.5 vvm), oxygen supplementation (max 33.3 lpm), and backpressure (max 12 psi). Foaming was controlled with Pluronic L-61 (25% v/v). When the OD of the culture reaches 10 U/mL a glycerol feed (50% v/v) is initiated at a flowrate of 45 mL/min. When OD reaches 40 U/mL, the cells are induced with the addition of IPTG to 0.2 mM final concentration.

5.7 Harvest

After 4 hours post-induction, the fermenter is chilled to 10° C. and the airflow and agitation are reduced to 0.3 vvm and 100 rpm respectively. Foam and pH controls are terminated and backpressure is adjusted to 3 psi. The culture is harvested by continuous centrifugation with a Westfalia CSA 8 continuous centrifuge at 10° C. The centrifuge is operated at 15,000 rpm and a flow rate of 3 liters per min and cell slurries collected.

5.8 Cell Lysis and IB Recovery

The fermentation cell paste (from Section 5.7) is diluted 1:5 with Lysis Buffer (6.1 g/L TrizmaBase (Tris), 3.7 g/L ethylenediaminetetraacetic acid (EDTA), 58.44 g/L NaCl and 10 g/L Triton X-100, pH 8.0) and re-suspended using a hand held homogenizer. The re-suspended cell paste is passed twice through a high-pressure homogenizer (parameters: pressure, 10,000 psig; flow rate, 450 mL/min; and temperature, 15° C.). The homogenised cell lysate is then centrifuged (bucket centrifuge, fixed-angle rotor) at 5,000×g for 20 minutes at 4° C. The supernatant is discarded leaving insoluble (inclusion bodies) TGF-β3. The inclusion body (IB) pellet is re-suspended in Wash Buffer (6.1 g/L Tris and 3.72 g/L EDTA, pH 8.0) using a hand held homogenizer and centrifuged (5,000×g for 20 minutes at 4° C.).

5.9 Inclusion Body Solubilization

The sediment from Section 5.8 is diluted 1:10 with Solubilization Buffer (6.1 g/L Tris, 15.4 g/L DL-dithiothreitol (DTT) and 360.4 g/L urea, pH 8.0) and re-suspended using a hand held homogenizer. The suspension is covered and left stirring for 60-75 minutes, at room temperature to solubilize the inclusion bodies and reduce TGF-β3 to its monomeric form. The pH of the re-suspended pellet is adjusted to pH 9.4-9.6 with NaOH/acetic acid before incubation for a second time for 60-75 minutes.

5.10 Clarification/Ultrafiltration and Diafiltration

Solubilized material from Section 5.9 is clarified, concentrated and dia-filtered in a Tangential Flow Filtration (TFF) system (Millipore). Initial clarification and concentration is achieved with a pre-conditioned clarification TFF membrane (Millipore Pellicon 1000 kDa, regenerated cellulose, screen V). The clarified TGF-β3 is collected in the permeate. Switching to a Ultrafiltration/Diafiltration (UF/DF) membrane (Millipore Pellicon 5 kDa, regenerated cellulose, screen C), the TGF-β3 is then washed in 6 diavolumes of Solubilisation Buffer (6.1 g/L Tris, 15.4 g/L DTT and 360.4 g/L urea, pH 9.5).

5.11 Ultrafiltration/Hydrophobic Interaction Chromatography.

The selected refolding solution is concentrated 5 fold by ultrafiltration (the membrane may be a flat-sheet Millipore Pellicon 5 kDa, 0.1 m$^2$, Regenerated Cellulose, screen). The pH of the concentrated re-fold material is then adjusted to a pH of 2.5-2.8 using glacial acetic acid before being diluted 1:1 in Dilution Buffer (2.72 g/L sodium acetate, 264.28 g/L ammonium sulfate, 100 g/L acetic acid, and 210.7 g/L arginine hydrochloride pH 3.3). A Butyl Sepharose 4 Fast Flow Column (Amersham, 16 cm Bed Height) is equilibrated with four column volumes of Buffer A (2.72 g/L sodium acetate, 132.14 g/L ammonium sulfate and 100 g/L acetic acid pH 3.3). The refold material is filtered through 0.22 µM membrane (Millipore Millipak filter) before being loaded onto the Butyl Sepharose column at a flow rate of 100 cm/hr (this flow rate was used throughout procedure). The column is then washed in Buffer A for four-column volumes. The TGF-Beta 3 proteins are eluted off the column using Buffer B (2.72 g/L sodium acetate, 100 g/L acetic acid and 300 g/L ethanol pH 3.3). The first peak, which contains TGF-β3 proteins in both monomeric and dimeric forms, is pooled, prior to separation of the monomeric and dimeric proteins.

Sequence Information

TGF-β3
(Sequence ID No. 1)
ALDTNYCFRNLEENCCVRPLYIDFRQDLGWKWVHEPKGYYANFCSGPCPY

LRSADTTHSTVLGLYNTLNPEASASPCCVPQDLEPLTILYYVGRTPKVEQ

LSNMVVKSCKCS

Mutant TGF-β3 "Gly63-Ala"
(Sequence ID No. 3)
ALDTNYCFRNLEENCCVRPLYIDFRQDLGWKWVHEPKGYYANFCSGPCPY

LRSADTTHSTVLALYNTLNPEASASPCCVPQDLEPLTILYYVGRTPKVEQ

LSNMVVKSCKCS

Mutant TGF-β3 "Gly63-Pro"
(Sequence ID No. 5)
ALDTNYCFRNLEENCCVRPLYIDFRQDLGWKWVHEPKGYYANFCSGPCPY

LRSADTTHSTVLPLYNTLNPEASASPCCVPQDLEPLTILYYVGRTPKVEQ

LSNMNVVKSCKCS

Mutant TGF-β3 "Glu12-Ser"
(Sequence ID No. 7)
ALDTNYCFRNLSENCCVRPLYIDFRQDLGWKWVHEPKGYYANFCSGPCPY

LRSADTTHSTVLGLYNTLNPEASASPCCVPQDLEPLTILYYVGRTPKVEQ

LSNMVVKSCKCS

Mutant TGF-β3 "Arg52-Ser"
(Sequence ID No.9)
ALDTNYCFRNLEENCCVRPLYIDFRQDLGWKWVHEPKGYYANFCSGPCPY

LSSADTTHSTVLGLYNTLNPEASASPCCVPQDLEPLTILYYVGRTPKVEQ

LSNMVVKSCKCS

Mutant TGF-β3 "Glu12-Ser/Arg52-Ser"
(Sequence ID No. 11)
ALDTNYCFRNLSENCCVRPLYIDFRQDLGWKWVHEPKGYYANFCSGPCPY

LSSADTTHSTVLGLYNTLNPEASASPCCVPQDLEPLTILYYVGRTPKVEQ

LSNMVVKSCKCS

Sequence ID No.2-
DNA encoding wild-type human TGF-β3
GCT TTG GAC ACC AAT TAC TGC TTC CGC AAC TTG GAG

GAG AAC TGC TGT GTG CGC CCC CTC TAC ATT GAC TTC

CGA CAG GAT CTG GGC TGG AAG TGG GTC CAT GAA CCT

AAG GGC TAC TAT GCC AAC TTC TGC TCA GGC CCT TGC

CCA TAC CTC CGC AGT GCA GAC ACA ACC CAC AGC ACG

GTG CTG GGA CTG TAC AAC ACT CTG AAC CCT GAA GCA

TCT GCC TCG CCT TGC TGC GTG CCC CAG GAC CTG GAG

CCC CTG ACC ATC CTG TAC TAT GTT GGG AGG ACC CCC

AAA GTG GAG CAG CTC TCC AAC ATG GTG GTG AAG TCT

TGT AAA TGT AGC

Sequence ID No.4-
DNA encoding Gly63-Ala mutant
GCT TTG GAC ACC AAT TAC TGC TTC CGC AAC TTG GAG

GAG AAC TGC TGT GTG CGC CCC CTC TAC ATT GAC TTC

CGA CAG GAT CTG GGC TGG AAG TGG GTC CAT GAA CCT

AAG GGC TAC TAT GCC AAC TTC TGC TCA GGC CCT TGC

GCA TAC CTC CGC AGT GCA GAC ACA ACC CAC AGC ACG

GTG CTG GCA CTG TAC AAC ACT CTG AAC CCT GAA GCA

TCT GCC TCG CCT TGC TGC GTG CCC CAG GAC CTG GAG

CCC CTG ACC ATC CTG TAC TAT GTT GGG AGG ACC CCC

AAA GTG GAG CAG CTC TCC AAC ATG GTG GTG AAG TCT

TGT AAA TGT AGC

Sequence ID No. 6-
DNA encoding Gly63-Pro mutant
GCT TTG GAC ACC AAT TAC TGC TTC CGC AAC TTG GAG

GAG AAC TGC TGT GTG CGC CCC CTC TAC ATT GAC TTC

CGA CAG GAT CTG GGC TGG AAG TGG GTC CAT GAA CCT

AAG GGC TAC TAT GCC AAC TTC TGC TCA GGC CCT TGC

CCA TAC CTC CGC AGT GCA GAC ACA ACC CAC AGC ACG

GTG CTG CCA CTG TAC AAC ACT CTG AAC CCT GAA GCA

TCT GCC TCG CCT TGC TGC GTG CCC CAG GAC CTG GAG

CCC CTG ACC ATC CTG TAC TAT GTT GGG AGG ACC CCC

AAA GTG GAG CAG CTC TCC AAC ATG GTG GTG AAG TCT

TGT AAA TGT AGC

Sequence ID No. 8-
DNA encoding Glu12-Ser mutant
GCT TTG GAC ACC AAT TAC TGC TTC CGC AAC TTG TCG

GAG AAC TGC TGT GTG CGC CCC CTC TAC ATT GAC TTC

CGA CAG GAT CTG GGC TGG AAG TGG GTC CAT GAA CCT

AAG GGC TAC TAT GCC AAC TTC TGC TCA GGC CCT TGC

CCA TAC CTC CGC AGT GCA GAC ACA ACC CAC AGC ACG

GTG CTG GGA CTG TAC AAC ACT CTG AAC CCT GAA GCA

TCT GCC TCG CCT TGC TGC GTG CCC CAG GAC CTG GAG

CCC CTG ACC ATC CTG TAC TAT GTT GGG AGG ACC CCC

AAA GTG GAG CAG CTC TCC AAC ATG GTG GTG AAG TCT

TGT AAA TGT AGC

Sequence ID No. 10-
DNA encoding Arg52-Ser mutant
GCT TTG GAC ACC AAT TAG TGC TTC CGC AAC TTG GAG

GAG AAC TGC TGT GTG CGC CCC CTC TAC ATT GAC TTC

CGA CAG GAT CTG GGC TGG AAG TGG GTC CAT GAA CCT

AAG GGC TAC TAT GCC AAC TTC TGC TCA GGC CCT TGC

CCA TAC CTC AGC AGT GCA GAC ACA ACC CAC AGC ACG

GTG CTG GGA CTG TAC AAC ACT CTG AAC CCT GAA GCA

TCT GCC TCG CCT TGC TGC GTG CCC CAG GAC CTG GAG

CCC CTG ACC ATC CTG TAC TAT GTT GGG AGG ACC CCC

AAA GTG GAG CAG CTC TCC AAC ATG GTG GTG AAG TCT

TGT AAA TGT AGC

Sequence ID No. 12-
DNA encoding Glu12-Ser/Arg52-Ser mutant
GCT TTG GAC ACC AAT TAC TGC TTC CGC AAC TTG TCG

GAG AAC TGC TGT GTG CGC CCC CTC TAC ATT GAC TTC

CGA CAG GAT CTG GGC TGG AAG TGG GTC CAT GAA CCT

AAG GGC TAC TAT GCC AAC TTC TGC TCA GGC CCT TGC

CCA TAC CTC AGC AGT GCA GAC ACA ACC CAC AGC ACG

GTG CTG GGA CTG TAC AAC ACT CTG AAC CCT GAA GCA

TCT GCC TCG CCT TGC TGC GTG CCC CAG GAC CTG GAG

CCC CTG ACC ATC CTG TAC TAT GTT GGG AGG ACC CCC

AAA GTG GAG CAG CTC TCC AAC ATG GTG GTG AAG TCT

TGT AAA TGT AGC

TABLE 1

A helix propensity scale based on experimental studies of proteins and peptides

| Amino acid | Helix propensity (kcal/mol) |
|---|---|
| Ala | 0.00 |
| Glu$^0$ | 0.16 |
| Leu | 0.21 |
| Met | 0.24 |
| Arg$^+$ | 0.21 |
| Lys$^+$ | 0.26 |
| Gln | 0.39 |
| Glu$^-$ | 0.40 |
| Ile | 0.41 |
| Asp$^0$ | 0.43 |
| Ser | 0.50 |
| Trp | 0.49 |
| Tyr | 0.53 |

TABLE 1-continued

A helix propensity scale based on experimental studies of proteins and peptides

| Amino acid | Helix propensity (kcal/mol) |
|---|---|
| Phe | 0.54 |
| Val | 0.61 |
| Thr | 0.66 |
| His$^0$ | 0.56 |
| His$^+$ | 0.66 |
| Cys | 0.68 |
| Asn | 0.65 |
| Asp$^-$ | 0.69 |
| Gly | 1.00 |
| Pro | 3.16 |

TABLE 2

| Mutant Nomenclature | Amino Acid Substitution | Effect on Structure |
|---|---|---|
| Gly63-Ala | Glycine 63 replaced with Alanine | Stabilises Alpha Helix |
| Gly63-Pro | Glycine 63 replaced with Proline | Destabilises Alpha Helix |
| Glu12-Ser | Glutamic acid 12 replaced with Serine | Prevents Salt Bridge Formation |
| Arg52-Ser | Arginine 52 replaced with Serine | Prevents Salt Bridge Formation |
| Glu12-Ser and Arg52-Ser | Double substitution in which Glutamic acid 12 is replaced with Serine and Arginine 52 is also replaced with Serine | Prevents Salt Bridge Formation |

TABLE 3

Re-folding Efficiency of wild-type TGF-β3 and TGF-β3s of the invention.

| TGF-Beta 3 Mutant | Percentage of Correctly folded Dimer |
|---|---|
| Gly63-Ala | 50 |
| 'Wild-Type' TGF-Beta 3 | 20 |
| Gly63-Pro | 1 |
| Glu12-Ser | 20 |
| Glu12-Ser & Arg52-Ser | 20 |

TABLE 4

Biological Activity of Wild-Type TGF-β3 and Gly63-Ala (a TGF-β3 Protein of the invention) Assessed by Cell Growth inhibition Assay

| Protein | IC$_{50}$ |
|---|---|
| 'Wild-Type' TGF-Beta 3 | 26 pg/mL |
| Gly63-Ala | 34 pg/mL |

TABLE 5

Wound site treatment.

| Group | Treatment/sample | Concentration (ng/100 μL) |
|---|---|---|
| A | 'Wild-type' TGF-Beta 3 | 50 |
| B | 'Wild-type' TGF-Beta 3 | 100 |
| C | Gly63-Ala | 50 |
| D | Gly63-Ala | 100 |
| E | Gly63-Pro | 50 |
| F | Gly63-Pro | 100 |
| G | 0.25M Maltose (Placebo Control) | N/A |
| H | No treatment (Naïve control) | N/A |

TABLE 6

Wound site treatment.

| Group | Treatment/sample | Concentration (ng/100 μL) |
|---|---|---|
| A | 'Wild-type' TGF-Beta 3 | 50 |
| B | 'Wild-type' TGF-Beta 3 | 100 |
| C | Gly63-Ala | 50 |
| D | Gly63-Ala | 100 |
| E | Gly63-Pro | 50 |
| F | Gly63-Pro | 100 |
| G | Glu12-Ser | 50 |
| H | Glu12-Ser | 100 |
| I | Glu12-Ser & Arg52-Ser | 50 |
| J | Glu12-Ser & Arg52-Ser | 100 |
| K | 0.25M Maltose (Placebo) | N/A |
| L | Naïve | N/A |

The invention claimed is:

1. An isolated TGF-β3 protein comprising a substitution or substitutions at the amino acid residues selected from the group consisting of (a) the glutamic acid residue at position 12, (b) the arginine residue at position 52, and (c) both the glutamic acid residue at position 12 and the arginine residue at position 52, wherein each of the substituted positions corresponds to the position in full-length wild type TGF-β3 as set forth in SEQ ID NO: 1.

2. An isolated TGF-β3 protein according to claim 1, wherein the substitution or substitutions is with an amino acid residue selected from the group consisting of a serine, an alanine, a threonine, a valine, an isoleucine, a methionine, a phenylalanine, and a leucine residue.

3. An isolated TGF-β3 protein according to claim 1, wherein the glutamic acid residue corresponding to position 12 of full-length wild type TGF-β3 as set forth in SEQ ID NO: 1 is substituted by a serine residue.

4. An isolated TGF-β3 protein according to claim 1, wherein the arginine residue corresponding to position 52 of full-length wild type TGF-β3 as set forth in SEQ ID NO: 1 is substituted by a serine residue.

5. An isolated TGF-β3 protein according to claim 1, wherein the amino acid sequence of the TGF-β3 protein is selected from the group consisting of SEQ ID NO: 7, SEQ ID NO: 9, and SEQ ID NO: 11.

6. A monomeric TGF-β3 protein according to claim 1.

7. A dimeric TGF-β3 protein according to claim 1.

8. A composition comprising a TGF-β3 protein according to claim 1, and a pharmaceutically acceptable vehicle.

* * * * *